(12) United States Patent
Konno et al.

(10) Patent No.: US 8,873,705 B2
(45) Date of Patent: Oct. 28, 2014

(54) X-RAY CT APPARATUS

(75) Inventors: Yasutaka Konno, Tokyo (JP); Fumito Watanabe, Tokyo (JP); Fuyuhiko Teramoto, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 552 days.

(21) Appl. No.: 13/377,603

(22) PCT Filed: Jun. 21, 2010

(86) PCT No.: PCT/JP2010/060422
§ 371 (c)(1),
(2), (4) Date: Dec. 12, 2011

(87) PCT Pub. No.: WO2010/150717
PCT Pub. Date: Dec. 29, 2010

(65) Prior Publication Data
US 2012/0093280 A1    Apr. 19, 2012

(30) Foreign Application Priority Data
Jun. 23, 2009    (JP) .................................. 2009-148867

(51) Int. Cl.
*A61B 6/03*    (2006.01)
*G01T 1/29*    (2006.01)

(52) U.S. Cl.
CPC .............. *A61B 6/032* (2013.01); *G01T 1/2985* (2013.01)
USPC .......................................................... 378/19

(58) Field of Classification Search
CPC ..................... A61B 6/03; G01T 1/24
USPC .......................................................... 378/19
See application file for complete search history.

(56) References Cited

U.S. PATENT DOCUMENTS

2003/0001077 A1*  1/2003  Perregaux .................. 250/208.1
2010/0150305 A1*  6/2010  Nowak et al. .................... 378/22

FOREIGN PATENT DOCUMENTS

| JP | 2001-242253 | 9/2001 |
| JP | 2004-8406 | 1/2004 |
| JP | 2009-118943 | 6/2009 |

OTHER PUBLICATIONS

PTO-14/0382 for English translation of Sato JP 2009-118943A.*
International Search Report in PCT/JP2010/060422.

* cited by examiner

*Primary Examiner* — Toan Ton
*Assistant Examiner* — John Corbett
(74) *Attorney, Agent, or Firm* — Cooper & Dunham LLP

(57) ABSTRACT

In order to improve the tiling workability in manufacturing an X-ray detector and provide a technology for acquiring high-quality reconstruction images, when aligning a plurality of detector blocks (or detector modules) in a slice direction, a distance between adjacent X-ray detection elements between detector blocks (inter-block distance) is not matched with a distance between adjacent detector elements within a detector block (intra-block distance). Instead, between reference positions when manufacturing each detector block, output values at the positions, the number of which is the same as the number of X-ray detection elements between the reference positions and which are spaced at equal intervals, are estimated from the acquired raw data. Projection data is generated from the position and the raw data.

18 Claims, 29 Drawing Sheets

(a)

(b)

(a)

(b)

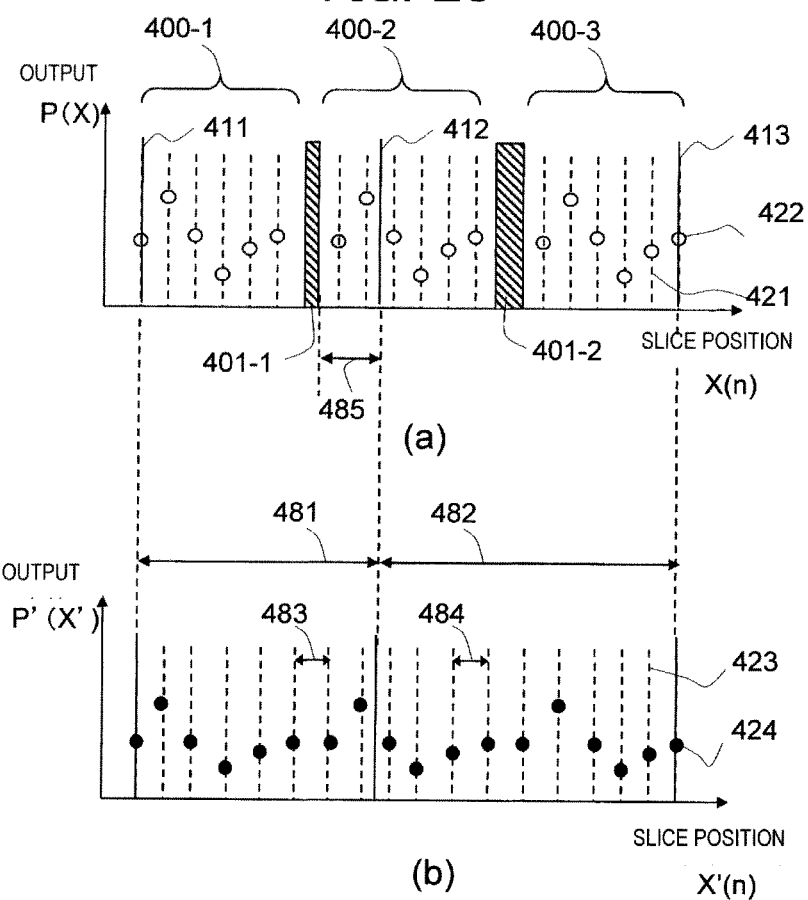

X-RAY CT APPARATUS

TECHNICAL FIELD

The present invention relates to a technique for improving the image quality of a reconstruction image in an X-ray CT apparatus and in particular, to an artifact reduction technique in a multi-slice X-ray CT apparatus including an X-ray detector with X-ray detection elements, which detect X-rays and are arrayed in a matrix.

BACKGROUND ART

The X-ray CT apparatus is an apparatus which obtains a tomographic image (hereinafter, described as a reconstruction image) of an object by calculating an X-ray absorption coefficient from an X-ray transmission image (hereinafter, described as projection data) of the object scanned from a plurality of directions, and is widely used in the medical or non-destructive inspection field. Especially in the medical field, the spread of multi-slice X-ray CT apparatuses has been progressing in recent years. The multi-slice X-ray CT apparatus acquires a plurality of reconstruction images by collecting the two-dimensional radiation data by one-time X-ray irradiation using an X-ray detector in which a plurality of detection element columns, each of which includes a plurality of X-ray detection elements arrayed in a channel direction along the surface of a reconstruction image, are arrayed in a slice direction, which is perpendicular to the channel direction, along the body axial direction of the object (for example, refer to PTL 1).

Since the multi-slice X-ray CT apparatus has such a structure, it is possible to photograph a wide field of view in the slice direction by one-time X-ray irradiation. Accordingly, a desired range can be scanned in a short time. As a result, not only can a photographing time be shortened, but also moving organs, such as the heart, can be scanned while suppressing blurring caused by the movement.

The X-ray detector of the multi-slice X-ray CT apparatus has a structure in which a semiconductor substrate formed with photoelectric conversion elements is mounted on a scintillator substrate which converts an X-ray into light. There is a tiling technique for realizing a desired number of X-ray detectors by forming detector blocks, the number of which is smaller than a predetermined number of stages, and arraying the plurality of detector blocks in the slice direction from the constraints of the size of a semiconductor substrate used, the difficulty of manufacturing, and the cost (for example, refer to PTL 2 and PTL 3).

CITATION LIST

Patent Literature

[PTL 1] JP-A-2000-316841
[PTL 2] JP-A-2001-242253
[PTL 3] JP-A-2004-215911

SUMMARY OF INVENTION

Technical Problem

In the case of realizing a desired number of X-ray detectors on one semiconductor substrate, X-ray detection elements are arrayed at equal intervals within the X-ray detector. When forming an X-ray detector by aligning a plurality of detector blocks, an interval between adjacent X-ray detection elements between the detector blocks needs to be equal to an interval between adjacent X-ray detection elements in each detector block in order that the plurality of detector blocks may have the same configuration. In order to do so, it is necessary to tile semiconductor substrates which form the detector blocks without a gap. However, this is technically difficult because it is necessary to completely remove the irregularities of end surfaces of the semiconductor substrates in order to make the end surfaces parallel to each other. In addition, since high technology is required, it becomes expensive. On the contrary, when tiling detection blocks without a gap is set as the premise of manufacturing, the positional accuracy of the tiling is reduced due to variations in manufacturing dimensions or irregularities at the end and the quality of a reconstruction image is also reduced accordingly.

In PTL 2, arraying X-ray detection elements at equal intervals is realized by making the width of a photoelectric conversion element at the semiconductor substrate end, which forms each detector block, shorter than the widths of photoelectric conversion elements at the other positions by a gap generated under the circumstances described above. In such a configuration, however, the light receiving area of the photoelectric conversion element at the end becomes smaller than that of the other photoelectric conversion elements. Accordingly, since a fill factor is reduced, the light receiving efficiency is lowered. In addition, since it is necessary to manufacture a photoelectric conversion element immediately before the end of the semiconductor substrate, the dark current characteristics or the photoelectric conversion efficiency of the photoelectric conversion element at the end may lower or vary compared with those in the other parts due to a crack or the like made when machining the end of the semiconductor substrate. In addition, similar to the semiconductor substrate, it is difficult to array adjacent scintillator element blocks without a gap. Accordingly, since high technology is required, it becomes expensive.

In addition, when a separator is provided between scintillator elements mounted on a scintillator substrate or a light reflecting layer is provided at the end of the scintillator substrate, equal-interval arrangement is realized by making thin the separator or the light reflecting layer at the end of each detector block. However, since these are made thin, light collection efficiency is lowered due to a reduction in the reflectance or a variation in the collection efficiency of X-ray detection elements is increased. In addition, when the equal interval is realized by adopting a configuration in which one light reflecting layer or separator is used in common in adjacent detector blocks, some light beams reflected by the separator or the light reflecting layer leak from a gap between both the detector blocks. As a result, the light collection efficiency is lowered.

The X-ray detector may be formed by further tiling a detector module, in which a scattered X-ray collimator is mounted, on a detector block. Also in this case, it is difficult to realize tiling without a gap. Moreover, in order to align X-ray detection elements at equal intervals, it is necessary to shorten the end of a support plate, which supports a scattered X-ray collimator plate, by the generated gap. Accordingly, support of the scattered X-ray collimator plate tends to be unstable.

The present invention has been made in view of the above, and it is an object of the present invention to provide a technique capable of improving the tiling workability in manufacturing an X-ray detector and acquiring a high-quality reconstruction image.

Solution to Problem

In the present invention, when aligning a plurality of detector blocks (or detector modules) in the slice direction, an interval between adjacent X-ray detection elements between detector blocks (inter-block distance) is not matched with an interval between adjacent detector elements within a detector block (intra-block distance). Instead, between the reference positions when manufacturing each detector block, output values at the positions, the number of which is the same as the number of X-ray detection elements between the reference positions and which are spaced at equal distances, are estimated from the acquired raw data. The projection data is generated from the position and the raw data.

Specifically, there is provided an X-ray CT apparatus including: X-ray generation means for irradiating X-rays; an X-ray detector in which a plurality of detector modules, each of which includes X-ray detection elements that detect the X-rays and convert the X-rays into electric signals and that are aligned in a two-dimensional direction of a channel direction and a slice direction, are arrayed in the slice direction; signal processing means for generating projection data by performing signal processing on raw data acquired from the electric signals detected by the plurality of X-ray detection elements of the X-ray detector; and reconstruction processing means for generating a reconstruction image by performing reconstruction processing on the projection data. Each of the detector modules has reference positions at predetermined positions in the slice direction. In the detector modules, there is a gap between the detector modules adjacent to each other in the slice direction. The signal processing means includes storage means for storing the width of the gap in the slice direction as a gap value, position correction means for correcting a slice position, which is specified by a position of the X-ray detection element of the X-ray detector, to a position set in advance between the reference positions set in two of the plurality of detector modules, and data estimation means for estimating a data output value at a slice position after correction by the position correction means from the gap value stored in the storage means and the raw data acquired from the electric signals detected by the X-ray detection elements, and generates the projection data from the data output value estimated by the data estimation means.

Advantageous Effects of Invention

According to the present invention, it is possible to acquire a highly precise reconstruction image while improving the tiling workability in manufacturing an X-ray detector.

BRIEF DESCRIPTION OF DRAWINGS

FIG. 1 is a schematic view of an X-ray CT apparatus of a first embodiment.

FIG. 2 is an external view of an X-ray detector of the first embodiment.

FIG. 3 is a sectional view of the X-ray detector of the first embodiment.

FIG. 4 is a view for explaining an example of a metal plate of a scattered X-ray collimator of the first embodiment.

FIG. 5 is a view for explaining an example of a metal plate support plate of the scattered X-ray collimator of the first embodiment.

FIGS. 6(a) to 6(c) are views for explaining an example of a method of manufacturing the X-ray detector of the first embodiment.

FIG. 7(a) is a functional block diagram of a central processing unit of the first embodiment, and FIG. 7(b) is a view for explaining the flow of data processing by the central processing unit of the first embodiment.

FIGS. 8(a) and 8(b) are views for explaining regular slice position calculation processing and output value estimation processing of the first embodiment.

FIG. 9 is a processing flow showing the flow of data processing of the first embodiment.

FIG. 10 is a processing flow for explaining the sensitivity data generation procedure of the first embodiment.

FIG. 11 is a processing flow for explaining the procedure of conversion coefficient calculation of the first embodiment.

FIG. 12 is a processing flow showing another example of the flow of the data processing of the first embodiment.

FIG. 13 is a processing flow showing another example of the flow of the data processing of the first embodiment.

FIG. 14 is a processing flow showing another example of the flow of the data processing of the first embodiment.

FIGS. 15(a) And 15(b) are views for explaining the advantages in performing position correction before reference correction in the first embodiment.

FIG. 16 is a processing flow showing another example of the flow of the data processing of the first embodiment.

FIG. 17 is a scanning diagram obtained when helical scanning of the first embodiment is performed.

FIG. 18 is a sectional view for explaining an example of the wiring structure of the detector module and the wiring substrate of the first embodiment.

FIG. 19 is a sectional view for explaining another example of a substrate alignment method of the first embodiment.

FIG. 20 is a sectional view for explaining another arrangement example of detector modules of the first embodiment.

FIG. 21 is a view for explaining an example of an X-ray detector with another X-ray detection element arrangement of the first embodiment.

FIGS. 22(a) and 22(b) are views for explaining position correction and an output value determination and calculation method of the first embodiment.

FIG. 23 is a view for explaining an example of the X-ray irradiation range on the X-ray detector of the first embodiment.

FIG. 24 is a view for explaining another example of the X-ray irradiation range on the X-ray detector of the first embodiment.

FIG. 25 is a flow showing an example of the flow of processing for changing the slice thickness of a reconstruction image in the first embodiment.

FIG. 26 is a flow showing another example of the flow of processing for changing the slice thickness of a reconstruction image in the first embodiment.

FIG. 27 is a sectional view of an X-ray detector of a second embodiment.

FIGS. 28(a) and 28(b) are views for explaining regular slice position calculation processing and output value estimation processing of the second embodiment.

[FIG. 29] FIGS. 29(a) and 29(b) are views for explaining another example of regular slice position calculation processing and output value estimation processing of the second embodiment

DESCRIPTION OF EMBODIMENTS

<<First Embodiment>>

Figure 1:
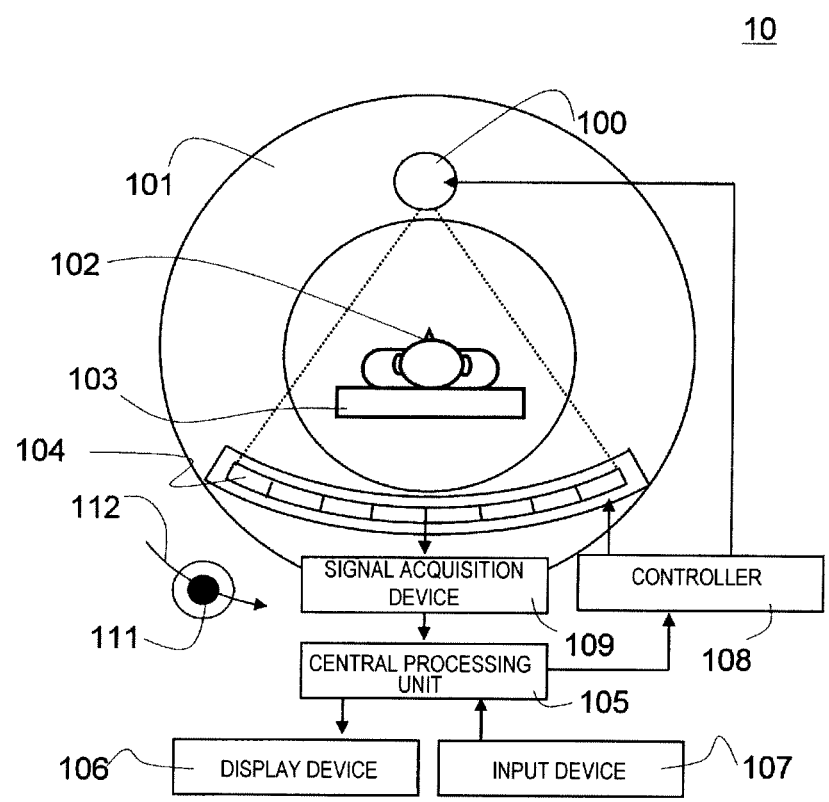
[FIG. 1]

Hereinafter, a first embodiment to which the present invention is applied will be described. Hereinafter, in all drawings for explaining the embodiments of the present invention, the same reference numeral is given to those with the same function, and repeated explanation thereof will be omitted. In addition, external views, sectional views, and explanatory views used for explanation of the embodiments are examples of the present invention and do not limit the present invention.

FIG. 1 is a schematic view of an X-ray CT apparatus of the present embodiment. As shown in this drawing, an X-ray CT apparatus 10 of the present embodiment includes: an X-ray source 100, an X-ray detector 104, a signal acquisition device 109, a central processing unit 105, a display device 106, an input device 107, a controller 108, a rotating table 101, and a top plate 103. A plurality of X-ray detectors 104 are arrayed in an arc shape with the X-ray source 100 as the approximate center, and are mounted in the rotating table 101 together with the X-ray source 100. Moreover, in this specification, the rotation direction of the X-ray source 100 and the rotating table 101 is called a channel direction 112, and the direction perpendicular to the rotation direction is called a slice direction 111.

In FIG. 1, a case where the eight X-ray detectors 104 are provided in the channel direction 112 is illustrated for simplicity of explanation. In the actual X-ray CT apparatus, about 40 X-ray detectors 104 are provided in the channel direction 112, for example. In addition, a scattered-X-ray collimator 120 (not shown herein; refer to FIG. 2 to be described later) is provided on the front of the X-ray detector 104. The scattered-X-ray collimator 120 prevents X-rays scattered by an object 102 or the like, among X-rays irradiated from the X-ray source 100, from being incident on the X-ray detector 104.

The central processing unit 105 controls the entire operation of the X-ray CT apparatus 10 of the present embodiment. When an instruction to start photographing is received through the input device 107, the controller 108 performs synchronous control of the irradiation of X-rays from the X-ray source 100 and the reading in the X-ray detector 104 and rotation control of the rotating table 101 according to an instruction from the central processing unit 105. The X-ray source 100 irradiates fan-shaped X-rays toward the object 102 placed on the top plate 103 according to an instruction from the controller 108. The X-ray detector 104 detects X-rays transmitted through the object 102 and converts them into electric signals. The signal acquisition device 109 collects the above electric signals and converts them into digital signals to generate raw data.

In addition, the central processing unit 105 generates projection data from the raw data and performs image processing on the projection data to generate a sectional image (reconstruction image) of the X-ray absorption coefficient distribution of the object 102. The display device 106 displays the generated reconstruction image. Moreover, in the present embodiment, the irradiation of X-rays is repeated while rotating the rotating table 101 in the rotation direction 112 to change the irradiation angle of X-rays with respect to the object 102, so that the raw data which can generate the projection data for 360° of the object 102 is collected. The collection of the raw data is performed every fixed rotation angle, for example, 0.4°. In addition, the raw data acquired at a certain rotation angle is called a view.

Figure 2:
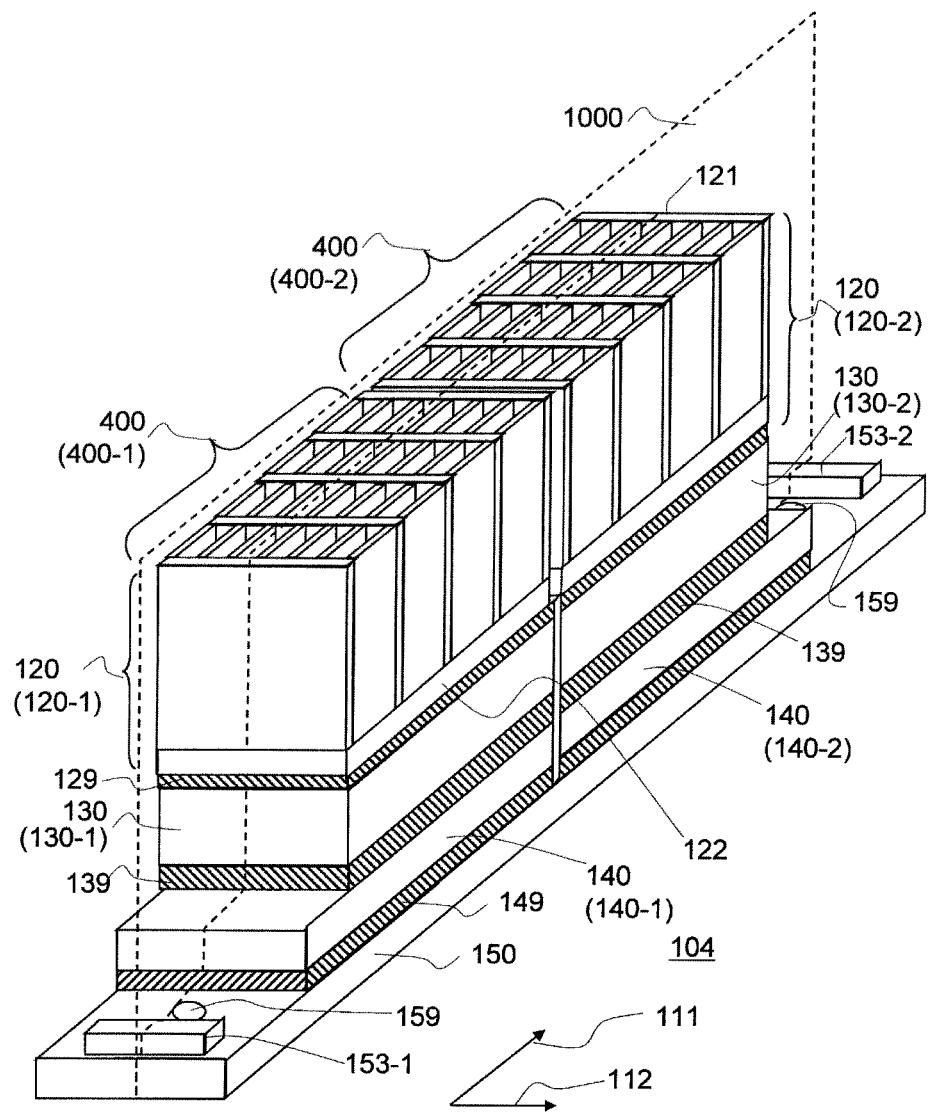
[FIG. 2]
Figure 3:
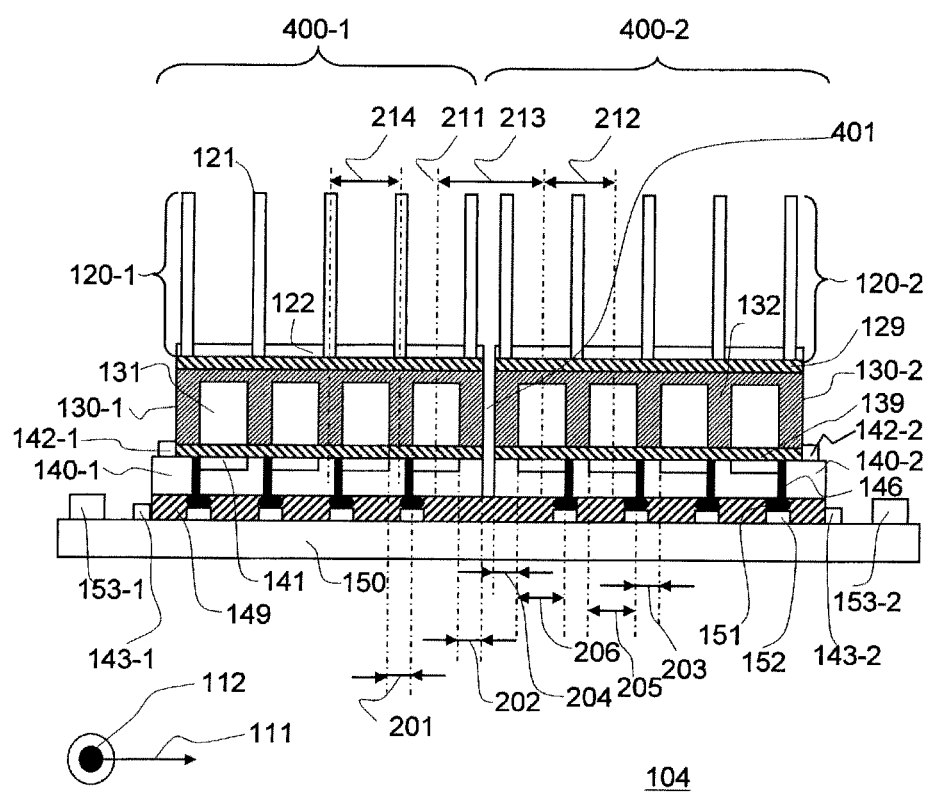
[FIG. 3]

Next, the structure of the X-ray detector 104 will be described using FIGS. 2 and 3. FIG. 2 is an external view for explaining an example of the appearance of the X-ray detector 104 of the present embodiment. In addition, FIG. 3 is a view for explaining an example of the sectional structure of the X-ray detector 104, and is a sectional view at a position 1000 in FIG. 2.

As shown in FIG. 2, the X-ray detector 104 of the present embodiment includes the scattered-X-ray collimator 120, a scintillator element substrate 130, a photoelectric conversion substrate (semiconductor substrate) 140, and a wiring substrate 150. The scattered-X-ray collimator 120 and the scintillator element substrate 130 are bonded to each other by an adhesive 129, the scintillator element substrate 130 and the photoelectric conversion substrate 140 are bonded to each other by an adhesive 139, and the photoelectric conversion substrate 140 and the wiring substrate 150 are bonded to each other by an adhesive 149. The plurality of X-ray detectors 104 are fixed to a detector fixing base (not shown) using a fixing hole 159, and are arrayed in the arc shape shown in FIG. 1.

The scattered-X-ray collimator 120 shields the incidence of X-rays scattered by the object 102 on the scintillator element. The scattered-X-ray collimator 120 is formed by metal plates 121 which are arrayed in parallel in each of both directions of the channel direction 112 and the slice direction 111 and are formed of tungsten and molybdenum, for example. These metal plates 121 are held by a metal plate support plate 122. The scintillator element substrate 130 includes scintillator elements 131 which are arrayed in a matrix and irradiate light when an X-ray is detected. The upper surface (surface on which X-rays are incident) and the side surface of the scintillator element substrate 130 between the scintillator elements 131 are covered with a light reflecting material 132 which reflects the fluorescence produced in the scintillator element 131. The photoelectric conversion substrate 140 includes a photoelectric conversion element 141 disposed on the surface facing the scintillator element substrate 130 so as to face the scintillator element 131. An electric signal from the photoelectric conversion element 141 is guided to an electrode pad 151, which is provided on the back surface (surface facing the wiring substrate 150) through a through wiring 146.

The photoelectric conversion element 141 and the scintillator element 131 form an X-ray detection element 161 (not shown) which detects an X-ray and generates an electric signal. The X-ray detection element 161 is disposed between the metal plates 121 of the scattered-X-ray collimator 120. In addition, the adhesive 139 by which the photoelectric conversion substrate 140 and the scintillator element substrate 130 are bonded to each other is transparent for light generated by the scintillator element 131 and connects the scintillator element 131 and the photoelectric conversion element 141 optically. Through the above configuration, among X-rays irradiated from the X-ray source 100, X-rays scattered by the object 102 are eliminated by the scattered-X-ray collimator 120 before being incident on the X-ray detection element 161, and X-rays transmitted through the object 102 are detected by the X-ray detection element 161 and converted into electric signals. In addition, X-rays of one slice in the slice direction 111 and one channel in the channel direction are detected for each X-ray detection element 161.

As shown in FIGS. 2 and 3, the scattered-X-ray collimator 120, the scintillator element substrate 130, and the photoelectric conversion substrate 140 are united to form one detector module 400. That is, the X-ray detector 104 of the present embodiment is formed by mounting the plurality of detector modules 400, which are arrayed adjacent to each other in the slice direction 111, on the wiring substrate 150. On the wiring substrate 150, an electrode pad 152 for electrical connection with the electrode pad 151 of the photoelectric conversion substrate 140 and a connector 153 for outputting an electric signal from the photoelectric conversion element 141 to the outside are connected to each other with wiring lines (not shown), as shown in FIG. 3.

Here, a case where the number of detector modules 400 is two will be described below as an example. When it is necessary to distinguish the two detector modules 400, detector module numbers of 1 and 2 are given to the two detector modules 400, respectively. Moreover, similar for each element which forms each detector module 400, these detector module numbers are added after the reference numeral when it is necessary to distinguish the elements. For example, in the case of the scattered-X-ray collimator 120, they are written as 120-1 and 120-2. In addition, the number of stages of the X-ray detection elements 161, which are arrayed in a matrix, in the slice direction 111 is called the number of slices, and the number of columns in the channel direction 112 is called the number of channels. In addition, in the present embodiment, a case where the X-ray detection elements 161 are arrayed at equal intervals in the slice direction 111 in one detector module 400 will be described as an example.

Next, an example of the procedure of manufacturing the X-ray detector 104 of the present embodiment will be described using FIGS. 4 to 6. However, the manufacturing procedure shown below is an example, and the present invention is not limited to this. In the present embodiment, the X-ray detector 104 is manufactured by forming the scattered-X-ray collimator 120, the scintillator element substrate 130, the photoelectric conversion substrate 140, and the wiring substrate 150 first, forming each detector module 400 using these, and mounting the formed detector module 400 on the wiring substrate 150.

Figure 4:
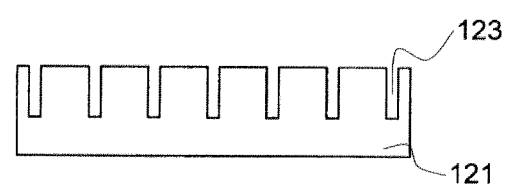
[FIG. 4]
Figure 5:
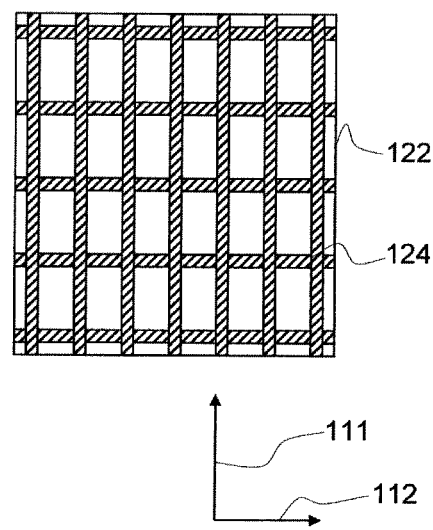
[FIG. 5]
Figure 6:
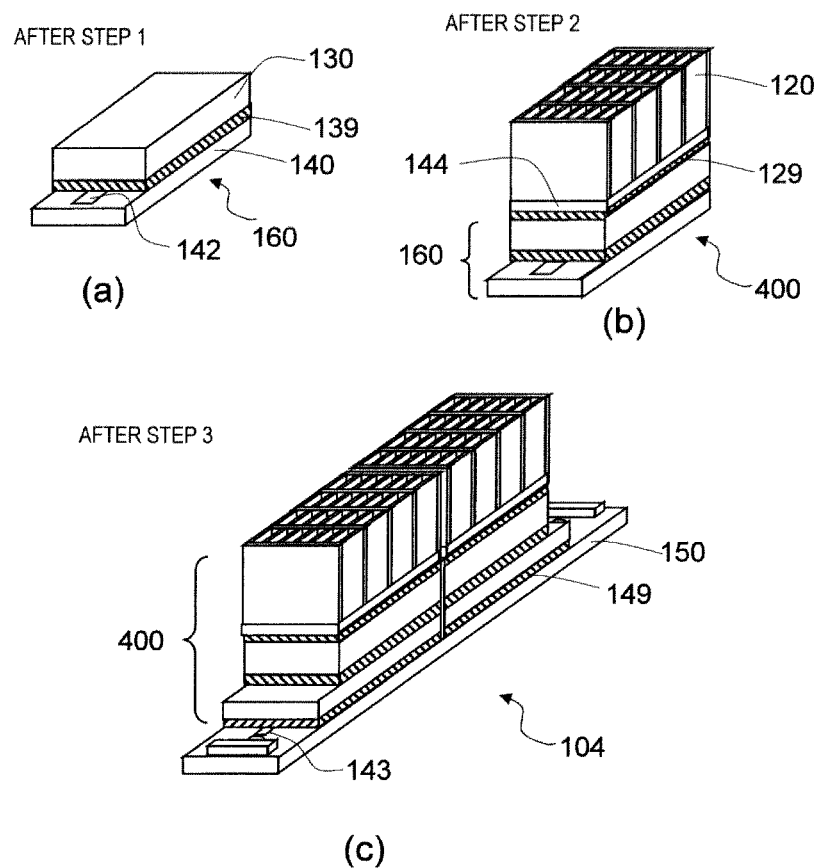
[FIG. 6]

For example, the scattered-X-ray collimator 120 is formed by mounting the metal plate 121 with a shape shown in FIG. 4 on the metal plate support plate 122 with a shape shown in FIG. 5. The metal plate 121 is formed of molybdenum or tungsten, for example, and has a recess 123. Here, FIG. 4 is an example of the metal plate 121 disposed in parallel to the slice direction 111 of the X-ray detector module 400 in which the number of channels is 6 and the number of slices is 4 (6 channels and 4 slices), and is an example including the seven recesses 123. In addition, the number of recesses 123 is determined by the number of channels and the number of slices of the X-ray detector module 400. For example, in the metal plate 121 disposed in parallel to the channel direction 112 of the X-ray detector module 400, the number of recesses 123 is 5. The metal plate support plate 122 is formed of a resin which has a good X-ray transmittance and does not deteriorate easily due to X-rays. The metal plate support plate 122 is preferably formed of polyethylene or acrylic, for example, and has a groove 124 shown in FIG. 5. During the assembly, first, the metal plate 121 for the channel direction is aligned in parallel to the channel direction 112 while being inserted into the groove 124 in a state where the recess 123 of the metal plate 121 for the channel direction aligned in parallel to the channel direction 112 faces upward. At this time, an adhesive is applied to the groove 124 in advance. Then, the metal plate 121 for the slice direction is aligned in parallel to the slice direction 111 while being inserted into the groove 124. At this time, the recess 123 of the metal plate 121 for the slice direction is placed downward so as to be engaged with the recess 123 of the metal plate 121 for the channel direction already inserted. Then, an adhesive is also applied to these crossing parts of the metal plates 121 to form the scattered-X-ray collimator 120. In addition, the above manufacturing procedure is an example, and the present invention is not limited to this.

The scintillator element substrate 130 is formed by cutting a scintillator plate formed of a material, such as GSO (Ce added Gd2SiO5 single crystal), LSO (Ce added Lu2SiO5 single crystal), BGO (Bi4Ge3O12), or CWO (CdWO4), in the channel direction and the slice direction and fixing the reflecting material 132 between the cut parts and the upper and side surfaces, for example.

The photoelectric conversion substrate 140 is formed by arraying the photoelectric conversion elements 141 on one surface (top surface) on a semiconductor substrate, such as crystalline silicon, and forming the electrode pad 151 on the other surface (back surface), for example. In addition, the through wiring 146 penetrating from the top surface to the back surface is formed. The photoelectric conversion element 141 is a PIN type or PN type photodiode, for example, and is formed using a general-purpose process. In addition, for example, in order to realize a large light receiving area, the photoelectric conversion element 141 is made to have a structure in which an electrode, a P layer, an N layer, and an l layer are vertically laminated on silicon. The electrode pad 151 is formed by vapor deposition, for example. The through wiring 146 is formed by generating a through hole on the semiconductor substrate by etching or the like first, forming an insulating layer in the through hole by a CVD method, a thermal oxidation method, or the like, and using a CVD method, a sputtering method, embedding of metal nanoparticles, or the like.

On the wiring substrate 150, the electrode pad 152 and wiring lines are formed on a substrate, such as a printed circuit board, a ceramic substrate, an aluminum substrate, and a Teflon (registered trademark) substrate, by a vapor deposition method, for example. In addition, the connector 153 is bonded by soldering, for example.

The process of manufacturing the X-ray detector 104 by assembling the respective substrates formed as described above will be described. FIGS. 6(a) to 6(c) are views showing an example of the process of manufacturing the X-ray detector 104. First, as shown in FIG. 6(a), an X-ray detection element substrate 160 is formed by bonding the scintillator element substrate 130 and the photoelectric conversion substrate 140 to each other with the adhesive 139 (step 1). Moreover, at this time, an end of the scintillator element substrate 130 is aligned with a marker 142 of the photoelectric conversion substrate 140. In addition, the end of the scintillator element substrate 130 aligned with the marker 142 when forming the X-ray detector 104 (detector module 400) becomes a reference position in position correction processing which will be described later.

Then, as shown in FIG. 6(b), the detector module 400 is formed by bonding the scattered-X-ray collimator 120 to the X-ray detection element substrate 160 formed in step 1 with the adhesive 129 (step 2). Here, at an end 144 at which the scintillator element substrate 130 is aligned with the marker 142 of the photoelectric conversion substrate 140, the end of the scattered-X-ray collimator 120 and the end of the scintillator element substrate 130 are aligned.

Then, as shown in FIG. 6(c), the two detector modules 400 are mounted on the wiring substrate 150 (step 3). At this time, in manufacturing of each of detector modules 400-1 and 400-2, the detector modules 400-1 and 400-2 are mounted such that the ends opposite the ends 144 whose positions are aligned in step 2 are adjacent to each other. In addition, the end of the photoelectric conversion substrate 140 is aligned with a marker 143 of the wiring substrate 150. In addition, each of the detector modules 400-1 and 400-2 and the wiring substrate 150 are bonded to each other by the adhesive 149, and the electrode pad 151 and the electrode pad 152 are electrically connected using a solder ball or the like, for example.

In the present embodiment, the X-ray detector 104 is formed according to the above steps. Therefore, since there is no step of performing special processing on the end of the detector module 400, the X-ray detector 104 is formed such that a thickness 201 of the light reflecting material 132 within the detector module 400 and a thickness 202 of the light reflecting material 132 at the end of the detector module 400 are equal and a width 206 of the scintillator element 131 at the end and a width 205 of the scintillator element 131 other than the end are equal, for example. However, there is a gap 401 between the detector modules 400. Here, the thickness 201 is also a distance 203 between the scintillator elements 131 within the detector module 400, and the thickness 202 is also a distance 204 from the scintillator element 131 to the end of the detector module 400. Hereinafter, in the present embodiment, a case where the distance 204 between the scintillator element 131 (X-ray detection element 161) of the end and the end of the detector module 400 is equal to the distance 201 between the scintillator elements 131 (X-ray detection elements 161) within the detector module 400 will be described as an example. Therefore, in the present embodiment, a distance 213 between centers 211 of the X-ray detection elements 161 adjacent to each other over the detector modules 400-1 and 400-2 (inter-element distance between modules) is larger by the gap 401 than a distance 212 between the centers of the X-ray detection elements 161 adjacent to each other within the detector module 400 (inter-element distance within a module).

Moreover, in each detector module 400 in the X-ray detector 104 of the present embodiment, a reference position at the time of manufacturing, that is, the marker 142 and the marker 143 are set on the opposite surface to the surface adjacent to the other detector modules 400. Therefore, the position can be determined accurately by the X-ray detector 161 near the opposite end to the adjacent surface of the detector module 400. Hereinafter, in the present embodiment, the surfaces of the two detector modules 400 adjacent to each other are called adjacent surfaces.

Figure 7:
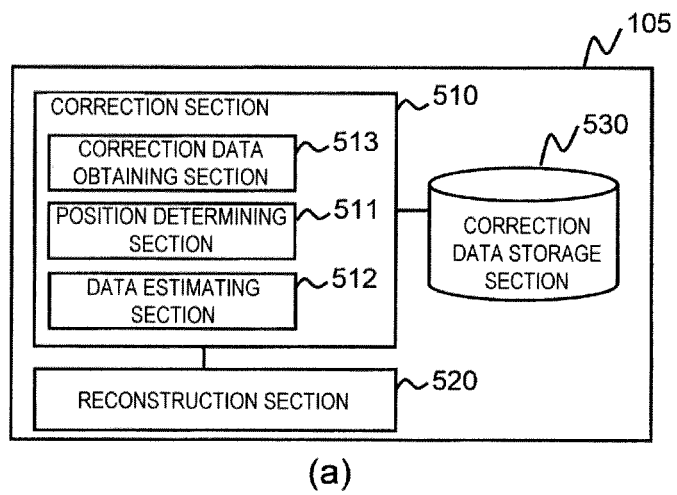
[FIG. 7]
Figure 7:
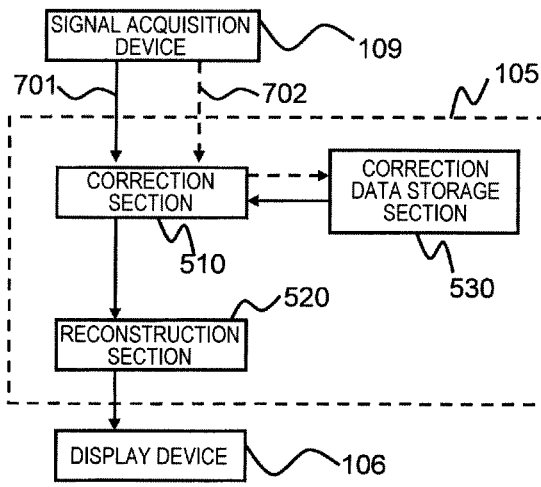

Next, data processing performed by the central processing unit 105 on the raw data obtained by converting an electric signal, which is detected by the X-ray detector 104 manufactured and configured as described above, into a digital signal by the signal acquisition device 109 will be described. In addition, in the present embodiment, FIG. 7(a) is a functional block diagram of the central processing unit 105 of the present embodiment. FIG. 7(b) is a view for explaining the flow of data processing in the central processing unit 105. As described above, the central processing unit 105 of the X-ray CT apparatus 10 of the present embodiment generates projection data from the raw data and performs image processing on the projection data to generate a reconstruction image. Accordingly, the central processing unit 105 includes a correction section 510 which generates the projection data from the raw data and a reconstruction section 520 which generates a reconstruction image from the projection data, as shown in FIG. 7(a). In addition, the central processing unit 105 includes a correction data storage section 530 which stores the correction data required when the correction section 510 performs correction processing.

The central processing unit 105 is formed by an information processing device including a CPU, a memory, and a storage device, and the correction section 510 and the reconstruction section 520 are realized when the CPU loads a program stored in the storage device to the memory and executing the program. In addition, the correction data storage section 530 is formed by a store device.

In FIG. 7(b), a solid line 701 shows the flow of data at the time of actual measurement, and a dotted line 702 show the flow of correction data. As shown in this drawing, the raw data generated by the signal acquisition device 109 is transmitted to the central processing unit 105. In the central processing unit 105, the correction section 510 performs correction processing on the raw data using the correction data to generate the projection data. Details of the raw data, the correction data, and the correction processing will be described later. Then, the reconstruction section 520 performs processing including convolution or back projection on the projection data to generate a reconstruction image. The generated reconstruction image is displayed on the display device 106.

The correction section 510 performs various kinds of correction on the raw data acquired by each X-ray detection element 161 to generate the projection data. In the present embodiment, since there is the gap 401 between the detector modules 400 as described above, the position of each X-ray detection element 161 deviates from the slice position (projection data point) assumed in the X-ray detector 104 formed by tiling without a gap. The correction section 510 of the present embodiment estimates the output value at the position after correcting this deviation from the raw data.

Accordingly, the correction section 510 includes a position determining section 511 which determines a slice position, which is assumed when a detector module as large as a predetermined ratio of each detector module 400 is tiled in the slice direction without a gap, and a data estimating section 512 which estimates the output value of the data of the position determined by the position determining section 511. That is, in the present embodiment, the slice position at which the raw data is actually acquired is corrected to the slice position determined by the position determining section 511, and the output value at the corrected slice position is estimated. For this reason, in this specification, the determination of the slice position by the position determining section 511 and the estimation of the output value by the data estimating section 512 are collectively called position correction processing hereinafter.

In addition, the slice position assumed when each detector module 400 is tiled in the slice direction without a gap is called a regular slice position, and the slice position at which the data is actually acquired is called an actual slice position. Here, the predetermined ratio is a ratio at which the reference position set in the detector modules 400 with a gap therebetween matches the reference position when detector modules are arrayed without a gap after multiplication of the predetermined ratio. In addition, the predetermined ratio includes ×1, and the detector module as large as the predetermined ratio of the detector module 400 may have the same size as the detector module 400.

In addition, the correction section 510 further includes a correction data obtaining section 513 which obtians data for generating the correction data used in correction processing. The correction data that the correction section 510 uses in correction processing is generated by performing necessary processing on the raw data, which is acquired by photographing the object 102 to generate the correction data by the correction data obtaining section 513, by the correction section 510. The generated correction data are stored in the correction data storage section 530. The photographing for generating the correction data is performed before the actual measurement. Details of the correction data will be described later.

When manufacturing the detector module 400 as described above, the position determining section 511 calculates a regular slice position using the reference position, the inter-element distance in a module 212 of the manufactured detector module 400, the gap 401 between the detector modules 400, and the number of slices. Such information used when the position determining section 511 calculates the regular slice position is stored in the correction data storage section 530 when manufacturing the X-ray detector 104. In the X-ray detector 104 of the present embodiment, since the inter-element distance in a module 212 is the same in each detector module 400, the regular slice positions are positions at which slices between the reference positions are arrayed at equal intervals. This can be realized by allocating the gap 401 to each interval while maintaining the ratio between the respective intervals and performing calculation, for example. Each interval is an interval between the reference position and the adjacent X-ray detection element 161, an interval between adjacent X-ray detection elements 161 in a module, and an interval between the gap and the adjacent X-ray detection element 161.

In addition, the data estimating section 512 of the present embodiment calculates the output value of each regular slice position from the raw data of two actual slice positions, which are adjacent to the regular slice position, by interpolation.

Figure 8:
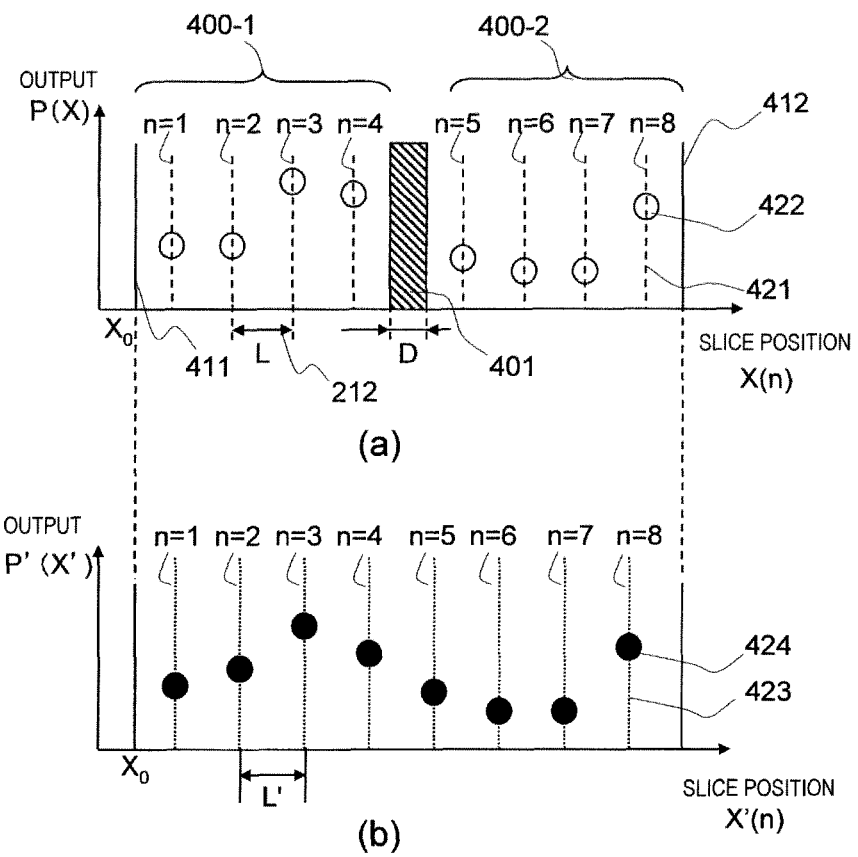
[FIG. 8]

Hereinafter, processing of the position determining section 511 and the data estimating section 512 of the present embodiment will be described through a specific example. FIG. 8 is a view for explaining the processing of calculating the regular slice position by the position determining section 511 of the present embodiment and the position correction processing by the data estimating section 512. Here, the horizontal axis indicates a position in the slice direction 111 in a certain channel, and the vertical axis indicates the value (output) of the raw data obtained from the output value of the X-ray detection element 161. FIG. 8(a) is an actual slice position and output value corresponding to each X-ray detection element 161 before position correction, and they are shown by a dotted line 421 and a white circle 422, respectively. FIG. 8(b) is a regular slice position and output value after position correction, and they are shown by a dotted line 423 and a black circle 424, respectively. In addition, here, a number is given to each slice in the slice direction 111. The actual slice position 421 of the n-th (n=1, 2, . . . , 8) slice is expressed as X(n) and the value of the raw data is expressed as P(n), and the regular slice position 423 of the n-th (n=1, 2, . . . , 8) slice is expressed as X'(n) and the output value is expressed as P'(n).

Here, n=1 to 4 are the X-ray detection elements 161 of the detector module 400-1, and n=5 to 8 are the X-ray detection elements 161 of the detector module 400-2. In addition, the region 401 is a gap between the detector modules 400-1 and 400-2. Here, it is assumed that the length (width) of the gap in the slice direction is D and the slice-direction length (interval) of the inter-element distance in a module 212 is L. In addition, the width D of this gap 401 is measured in advance by each X-ray detector 104 and is stored in the correction data storage section 530 as gap value data 902 (will be described later). The width D of the gap 401 is optically measured by a microscope, for example. In addition, it may be calculated from the output data indicating a predetermined change in the slice direction 111 which is obtained by photographing a phantom with an inclination in the slice direction 111.

Moreover, in the present embodiment, positions which are ends of the detector modules 400-1 and 400-2 and set as the reference positions when manufacturing the X-ray detector 104 (detector module 400) are used as reference positions 411 and 412 used to calculate the regular slice position, as shown in this drawing. That is, each distance between the reference positions 411 and 412 and the X-ray detection element 161 closest to the reference positions 411 and 412 is L/2. In this case, assuming that the position coordinates of one reference position in the slice direction are X0, each actual slice position X(n) shown in FIG. 8(a) is expressed as the following Expression (1).

[Expression 1]

$$X(n) = X_0 + L\left(n - \frac{1}{2}\right) (n = 1, 2, 3, 4) \quad (1)$$

$$X(n) = X_0 + L\left(n - \frac{1}{2}\right) + D (n = 5, 6, 7, 8)$$

On the other hand, each regular slice position X'(n) shown in FIG. 8(b) is arrayed at equal intervals without the gap 401, for example. As described above, this can be realized by allocating the width D of the gap 401 to all intervals while maintaining the ratio, for example. Therefore, each interval between slice positions L' in FIG. 8(b) becomes L+D/M, and the regular slice position X'(n) is expressed as the following Expression (2). In addition, M is the number of X-ray detection elements 161 (the number of slices) between the reference positions 411 and 412, and is 8 in FIG. 8(b).

[Expression 2]

$$X'(n) = X_0 + \left(L + \frac{D}{M}\right)\left(n - \frac{1}{2}\right) \quad (2)$$

The data estimating section 512 estimates the output value P'(n) at the regular slice position X'(n) (n=1, 2, . . . , 8) calculated in Expression (2). The estimation is calculated from the output values of the adjacent actual slice positions using a polynomial interpolation function, for example. For example, in the case of first-order polynomial, the output value P'(n) is calculated by the polynomial shown in the following Expression (3).

[Expression 3]

$$\text{When } n = 1, 2, 3, 4 \quad (3)$$
$$P'(n) = \frac{X(n+1) - X'(n)}{X(n+1) - X(n)} P(n) + \frac{X'(n) - X(n)}{X(n+1) - X(n)} P(n+1)$$
$$\text{When } n = 5, 6, 7, 8$$
$$P'(n) = \frac{X(n) - X'(n)}{X(n) - X(n-1)} P(n-1) + \frac{X'(n) - X(n-1)}{X(n) - X(n-1)} P(n)$$

Figure 9:
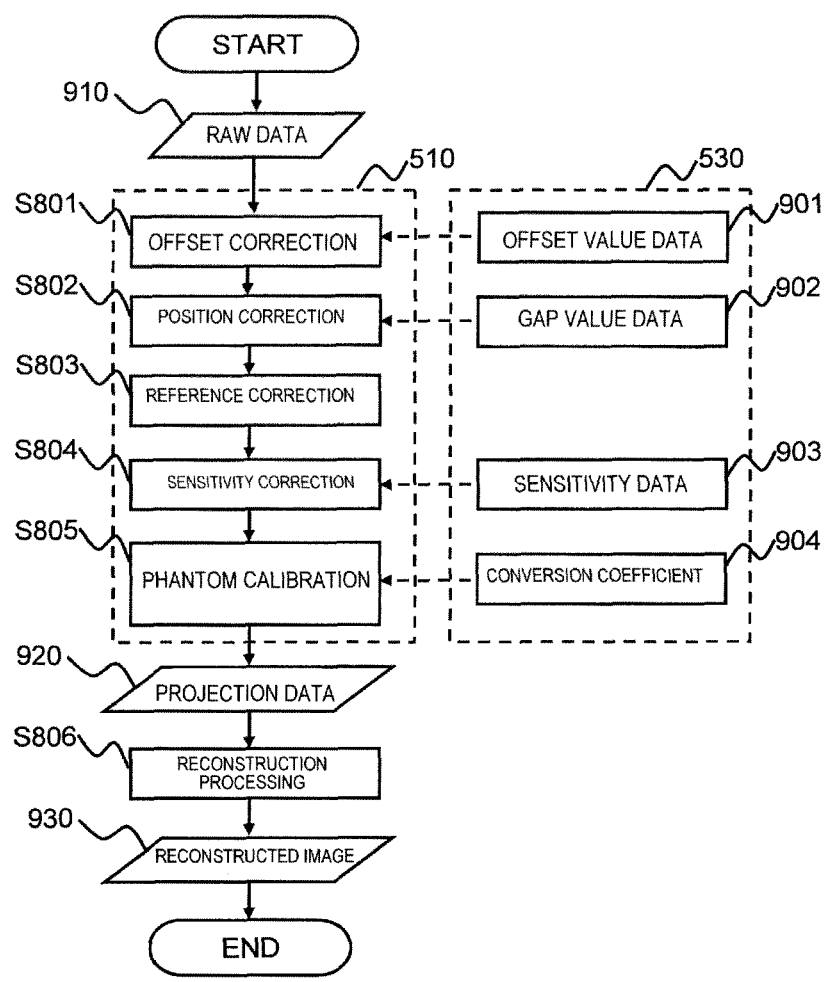
[FIG. 9]

Next, details of the correction processing by the correction section 510 will be described using FIG. 9. FIG. 9 is an explanatory view for describing an example of the flow of data processing by the central processing unit 105 of the present embodiment including the correction processing and the reconstruction processing by the reconstruction section 520. In addition to the position correction processing described above, the correction section 510 of the present embodiment performs offset correction processing, reference correction processing, sensitivity correction processing, and phantom calibration. Hereinafter, details of each processing will be described in accordance with details of the acquisition of the required correction data 203.

After finishing collection of all items of raw data 910 required when the signal acquisition device 109 generates a reconstruction image, the correction section 510 starts correction processing. However, this is an example and does not limit the present embodiment. For example, it is possible to start correction processing of the acquired raw data during the collection of the raw data. In the correction processing, offset correction processing is performed first (step S801). In the offset correction processing, a deviation of an output level caused by a leakage current of a read circuit and the photoelectric conversion element 141 or the like is corrected. The offset correction processing is performed by subtracting offset value data 901 acquired in advance from the raw data acquired by actual measurement. In addition, the offset value data 901 is generated by performing measurement for acquisition of raw data without irradiating an X-ray, for example, immediately before the actual measurement by the correction data obtaining section 513 and taking the average of the obtained raw data, and is stored in the correction data storage section 530.

After the offset correction processing, the correction section 510 performs position correction processing using the gap value data 902 (step S802). In the position correction processing, the correction section 510 determines a regular slice position for the raw data after offset correction by the above-described method and calculates the output value of the regular slice position.

The correction section 510 performs reference correction processing on the output value at the regular slice position (step S803). The reference correction processing is for correcting a temporal change in the X-ray intensity. The influence of an X-ray intensity change for each slice is eliminated by dividing the actual measurement data by the amount of X-rays (X-ray intensity parameter) which are not transmitted through the object 102.

For example, the X-ray intensity parameter is generated using the raw data acquired by the plurality of X-ray detection elements 161 located at the channel-direction end, among the X-ray detectors 104 aligned in the arc shape shown in FIG. 1, at the time of actual measurement. That is, the same correction processing as for the actual measurement data is performed on the raw data acquired for each slice and addition in the channel direction is performed, and this is set as the X-ray intensity parameter of each slice. For all views, the reference correction processing is performed for each slice in a view unit.

In addition, although the X-ray intensity parameter is calculated using the raw data acquired by the X-ray detection element 161 used at the time of actual measurement herein, the present invention is not limited to this. For example, the X-ray detection element 161 for acquiring the raw data for calculation of the X-ray intensity parameter may be provided separately from the X-ray detection element used for actual measurement.

The correction section 510 performs sensitivity correction for the output value after the reference correction processing (step S804). In the sensitivity correction, the correction section 510 corrects a positional difference of the X-ray distribution in the X-ray CT apparatus 10 or a sensitivity difference in each X-ray detection element 161. The correction section 510 corrects a variation in the output ratio (sensitivity) of X-rays for each X-ray detection element 161 by dividing the actual measurement data by sensitivity data 903 acquired in advance.

Figure 10:
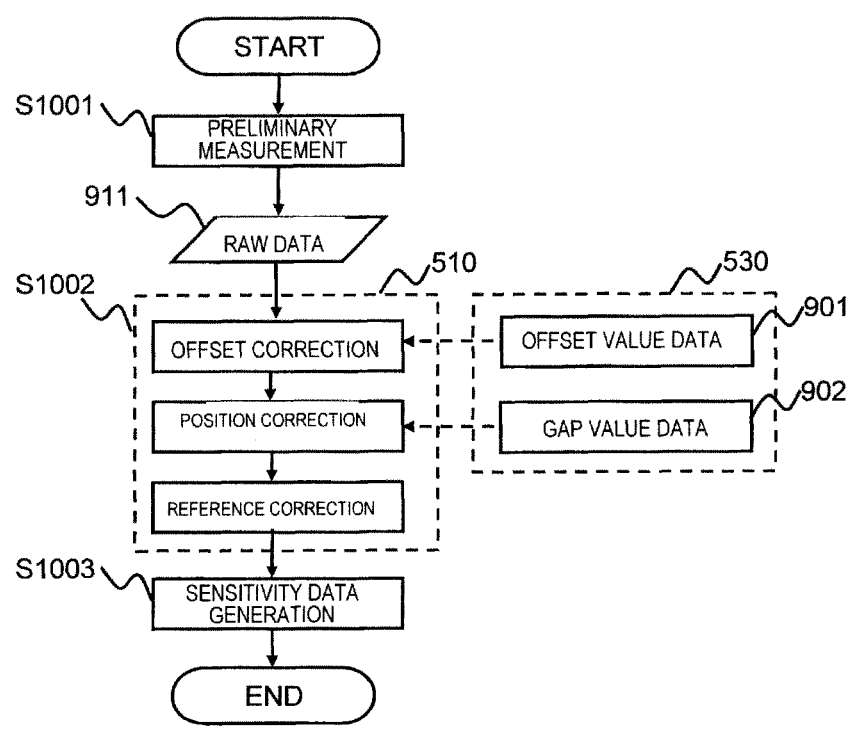
[FIG. 10]

The sensitivity data 903 is generated from raw data 911, which is obtained by sensitivity data acquisition measurement performed before the actual measurement, by the correction data obtaining section 513. FIG. 10 is a view for explaining the sensitivity data generation procedure by the correction data obtaining section 513. As shown in this drawing, the raw data 911 is acquired first without placing the object 102 (step S1001). Then, the correction section 510 performs the same correction as for the actual measurement data, which is to be corrected, on the acquired raw data 911 (step S1002). Here, since the offset correction processing, the position correction processing, and the reference correction processing are performed on the actual measurement data to be corrected before performing the sensitivity correction, the offset correction processing, the position correction processing, and the reference correction processing are also performed similarly on the raw data 911 acquired to generate the sensitivity data. Then, the correction data obtaining section 513 generates the sensitivity data 903 by calculating the average of addition in the view direction for each data item after correction for each channel and slice (step S1003). The correction data obtaining section 513 stores the acquired sensitivity data 903 in the correction data storage section 530.

After the sensitivity correction, the correction section 510 performs phantom calibration (step S805). The phantom calibration is for correcting a change of the X-ray absorption coefficient caused by beam hardening occurring when an X-ray is transmitted through the object, and the raw data acquired by measurement is multiplied by a conversion rate calculated from a conversion coefficient. By the phantom calibration, quantification of a reconstruction image is improved. As a result, an artifact is reduced or eliminated. A conversion coefficient 904 used in the phantom calibration is generated in advance by the correction data obtaining section 513 and is stored in the correction data storage section 530.

Figure 11:
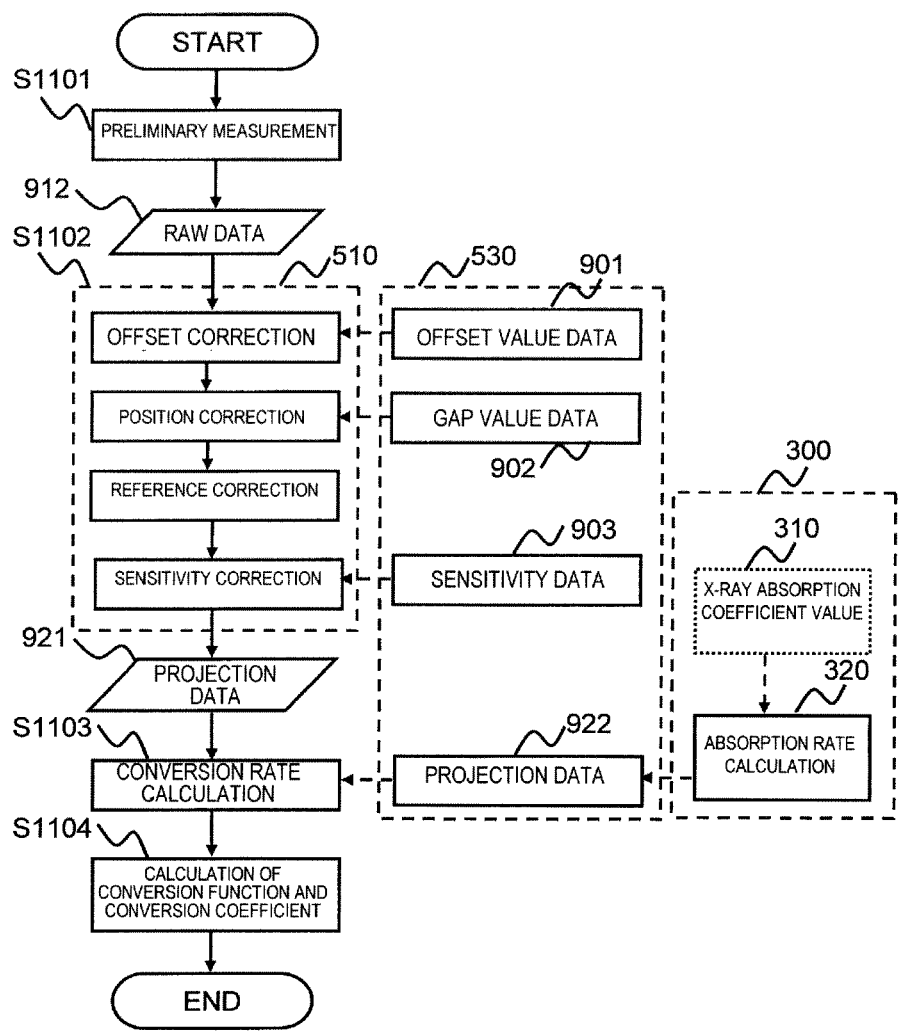
[FIG. 11]

Here, the generation of a conversion coefficient will be described. The conversion coefficient is for calculating a conversion rate, which corresponds to the absorption amount of X-rays and which is a ratio of the X-ray absorption rate when beam hardening is taken into consideration and the X-ray absorption rate when beam hardening is not taken into consideration, for each transmission distance, and is calculated from raw data 912 acquired by conversion coefficient acquisition measurement performed before the actual measurement. FIG. 11 is a view for explaining the procedure of conversion coefficient calculation by the correction data obtaining section 513 of the present embodiment. In order to measure an X-ray absorption coefficient change according to the transmission distance, the correction data obtaining section 513 performs measurement using a plurality of phantoms with different X-ray transmission distances to acquire the raw data 912 (step S1101). As a plurality of phantoms with different X-ray transmission distances, for example, phantoms which are formed of the same material and which have cylindrical shapes and different diameters are used. Then, the correction section 510 acquires projection data 921 for each transmission distance by performing the same correction as for the actual measurement data, on which the phantom calibration is performed, on the acquired raw data 912 (step S1102). Here, since the offset correction processing, the position correction processing, the reference correction processing, and the sensitivity correction processing are performed on the actual measurement data, on which the phantom calibration is performed, before the phantom calibration, the offset correction processing, the position correction processing, the reference correction processing, and the sensitivity correction processing are also performed similarly on the acquired raw data.

Then, the correction data obtaining section 513 calculates projection data 922 of each phantom when the hardening does not occur. The projection data 922 is calculated by performing known absorption rate calculation 320 from an X-ray absorption coefficient value 310 using a simulator 300. Here, the absorption coefficient distribution in the channel direction is calculated. The correction data obtaining section 513 calculates the ratio between the projection data 921 for each transmission distance acquired by photographing of the phantom and the projection data 922 acquired by the calculation and calculates the ratio as a conversion rate for each transmission distance (step S1103). Then, the correction data obtaining section 513 calculates a conversion coefficient function, which has a transmission distance as a variable, and the conversion coefficient 904 by performing polynomial approximation on the conversion rate for each measured transmission distance (step S1104). The conversion coefficient function and the conversion coefficient 904 for each transmission distance which have been acquired are stored in the correction data storage section 530.

In addition, since a cylindrical phantom is used in the above calculation of the conversion coefficient, the calculated distribution can be used in common for all slices. However, the shape of a phantom is not limited to this. For example, a conic phantom may also be used. In this case, the rotary axis of the cone is disposed in parallel to the slice direction 111 to perform measurement. In this case, since the shape (diameter of the cross section) changes with each slice, the absorption coefficient distribution is calculated for each slice.

In addition, in the case of a shape in which the transmission distance does not change in the slice direction 111 like the cylindrical phantom, the influence of the position correction processing is small. On the other hand, when the transmission distance changes in the slice direction like the conic phantom, the influence of the position correction processing is large. Therefore, in the absorption rate calculation 320 when acquiring the projection data 922 by calculation, which is shown in FIG. 11, it is necessary to take the gap 401 into consideration. That is, in the case of a conic phantom, each shape of the surface scanned at each slice position becomes a circle, but the radius changes due to the gap 401. Accordingly, the projection data 922 is calculated using the radius at the regular slice position.

Through the above procedure, the correction section 510 corrects the raw data 910 to generate projection data 920 which is an output value at the regular slice position (projection data point). The reconstruction section 520 performs the above-described reconstruction processing on the generated projection data 920 to generate a reconstruction image 930.

As described above, in the position correction processing of the present embodiment, the positions 411 and 412 which are the respective ends of the detector modules 400-1 and 400-2 are set as the reference, a regular slice position is calculated between the positions, and the output value P at the position is estimated from the adjacent value. For example, in the present embodiment, the output values at the slice positions arrayed at equal intervals between both ends can be acquired by the X-ray detector 104. In addition, all regular slice positions X'(n) (n=1, 2, . . . , 8) are located between the actual slice positions X(n) and X(n+1) or between the actual slice positions X(n−1) and X(n). For this reason, in the present embodiment, the output value P'(n) of the regular slice position X'(n) can be calculated from the output value P(n) of the actual slice position by interpolation without performing extrapolation. Therefore, it can be estimated accurately.

In addition, in the present embodiment, since the reference position when manufacturing the X-ray detector 104 is used as a reference for position correction, high-accuracy correction can be realized.

Therefore, according to the present embodiment, projection data of the same slice interval as when the X-ray detector 104 is formed by the one detector module 400 in the slice direction can be acquired with high precision. Since an image is reconstructed from such projection data, a reconstruction image after removing or reducing an artifact can be realized according to the present embodiment.

According to the present embodiment, when generating the projection data from the raw data, the correction section 510 performs the position correction processing as described above. Therefore, even if there is the gap 401 between the detector modules 400 when manufacturing the X-ray detector 104, the artifact of the reconstruction image can be reduced. Accordingly, since high accuracy is not required for manufacturing the X-ray detector 104 and the detector module 400, which forms the X-ray detector 104, and the constraints are reduced, the manufacturing becomes easy. In addition, since the tiling accuracy of the detector module 400 is not required either when manufacturing the X-ray detector 104, the manufacturing also becomes easy at this point. In addition, since the manufacturing becomes easy, the manufacturing cost is also reduced.

In addition, since it is not necessary to perform special processing on the end of the detector module 400, the mechanical stability at the end is improved and the characteristics of the X-ray detection element 161 at the end, such as light receiving efficiency, dark current characteristic, photoelectric conversion efficiency, X-ray use efficiency, light collection efficiency, and scattered ray removal efficiency, do not deteriorate.

Specifically, in the present embodiment, it is not necessary to make a study for making the interval between the X-ray detection elements 161 between the detector modules 400 equal to the interval between the X-ray detection elements 161 in the detector module 400 at the time of manufacturing. In the present embodiment, the plurality of detector modules 400 are arrayed in the slice direction 111 with the gap 401 therebetween. That is, the manufacturing can be done such that the distance 213 between the centers 211 of the X-ray detection elements adjacent to each other over the detector modules 400-1 and 400-2 is larger than the distance 212 between the centers 211 of the X-ray detection elements within the detector module 400. Such a structure has the following advantages.

First, the gap 401 of the sufficient width can be realized. Accordingly, even if the one detector module 400-1 has irregularities or distortion on the surface adjacent to the other detector module 400-2, the two detector modules 400-1 and 400-2 can be mounted with high precision without causing positional deviation since the gap 401 can be used as the allowance. Similarly, even if each of the scattered-X-ray collimator 120, the scintillator element substrate 130, and the photoelectric conversion substrate 140 which form the detector module 400 has irregularities or distortion, the two detector modules 400-1 and 400-2 can be mounted with high precision without causing positional deviation. Therefore, since there is no need of performing the manufacturing of the scattered-X-ray collimator 120, the scintillator element substrate 130, and the photoelectric conversion substrate 140 and the assembling of the detector module 400 with high precision, the X-ray detector 104 can be realized cheaply and easily by tiling.

In addition, in the scintillator element substrate 130, the reflecting material 132 with a sufficient thickness can be realized. In the related art, in order to make the inter-element distance between modules 213 equal to the inter-element distance in a module 212, it was necessary to set the thickness 202 of the reflecting material 132 at the end of the detector module 400 to the half or less of the thickness 201 of the reflecting material 132 within the detector module 400. In addition, since it was substantially impossible to dispose the scintillator element substrates 130-1 and 130-2 so as to be adjacent to each other without a gap, it was necessary to set the thickness 202 less than the half of the thickness 201. In the X-ray detector 104 of the present embodiment, however, it is possible to realize a sufficient thickness in which the thickness 202 is the half or more of the thickness 201 or the same as the thickness 201. Therefore, it is possible to avoid a sensitivity reduction occurring since the thickness of the reflecting material 132 is not sufficient and accordingly, light irradiated from the X-ray detection element at the end escapes from the gap of the end to the outside.

In addition, according to the present embodiment, in the scintillator element substrate 130, it is not necessary to make the width 206 of the scintillator element 131 at the end narrower than the width 205 of the scintillator element 131 at other positions. In addition, in the photoelectric conversion substrate 140, it is not necessary to make the width of the photoelectric conversion element 141 at the end narrower than the width of the photoelectric conversion element 141 at other positions. Therefore, it is possible to prevent a lowering in the X-ray use efficiency or the light collection efficiency due to a reduction in the detection area of X-rays or light.

In addition, according to the present embodiment, it is not necessary to make the inter-element distance between modules 213 and the inter-element distance in a module 212 equal to each other. For this reason, in the photoelectric conversion substrate 140, the photoelectric conversion element 141 of the X-ray detection element 161 at the end of one detector module 400-1 which is closest to the adjacent surface of the other detector module 400-2, can be realized at the position sufficiently separated from the end and with the same size as other elements. Until now, in order to make the inter-element distance between modules 213 equal to the inter-element distance in a module 212 and make the width 206 of the scintillator element 131 at the end equal to the width 205 of the scintillator element 131 at other positions, it was necessary to set the distance 204 from the scintillator element 131 to the end to the half or less of the distance 203 between the scintillator elements 131 in the detector module 400. In addition, since it was substantially impossible to dispose the photoelectric conversion substrate 140-1 and 140-2 so as to be adjacent to each other without a gap, it was necessary to set the distance 204 less than the half of the distance 203. However, since cracking or the like due to processing may occur at the end of the photoelectric conversion substrate 140, the photoelectric conversion element 141 at the end has a large dark current and low photoelectric conversion efficiency and these physical characteristics change compared with the photoelectric conversion element 141 at other positions. This reduced the yield further. According to the X-ray detector 104 of the present embodiment, however, these problems can be solved since the photoelectric conversion element 141 can be manufactured at the position sufficiently separated from the end of the photoelectric conversion substrate 140.

In addition, in the scattered-X-ray collimator 120, since the thickness of the metal plate 121 at the end can be made equal to that at other positions, a lowering in the scattered ray removal efficiency can be prevented. In addition, since a protruding structure which supports the metal plate 121 can be realized at the end, when necessary, the stability of scattered X-ray collimator plate support can be improved.

In order to realize the above advantages, it is preferable to determine the width D of the gap 401 in consideration of the accuracy of machining, manufacturing, and assembling of the detector module 400 or the constituent substrate. For example, it is preferable that the width D of the gap 401 be a width of 50 μm or more. In addition, in consideration of the required accuracy of position correction and the required resolution, it is preferable to set the width D of the gap 401 to 50% or less of the inter-element distance in a module.

Moreover, in the present embodiment, as shown in FIGS. 2 and 3, the X-ray detector 104 of six channels and eight slices is realized by tiling two detector modules 400 having X-ray detection elements 161 of six channels and four slices. The numbers of channels, the number of slices, and the detector module 400 are examples, and these are not limited to the above. For example, the X-ray detector 104 may be formed by tiling the three or more detector modules 400 in the slice direction.

In this case, in the position determining section 511, a regular slice position is determined within two reference positions set in advance such that each interval between slice positions is equal. For example, the regular slice position is determined by allocating the sum of the gap between the detector modules 400 to all intervals while maintaining each ratio. In addition, as the reference position, a reference position when manufacturing the two detector modules 400 arrayed at both ends in the slice direction is used. In addition, the output value P'(n) of the detector module 400 during the estimation of the data estimating section 512 can be calculated by the above-described Expression (3).

In addition, when there are three or more detector modules 400 in the slice direction, the gap value data 902 indicating the width D of the gap 401 is stored in the correction data storage section 530 so as to match each gap 401 between the detector modules 400. However, the present invention is not limited to this. For example, the width D of the gap 401 may be fixed in all detector modules 400, so that only one information item is stored. In addition, the width D of the gap 401 may be fixed in some of the detector modules 400, so that only one information item is stored for the detector modules 400 in which the width D of the gap 401 is fixed. For example, when a variation in the width D of the gap 401 is small or when the absolute value of the width D of the gap 401 is small, the width D of the gap 401 is treated as a fixed value. In addition, the gap value data 902 may be provided for each channel. For example, when the width D of the gap 401 changes with each channel, position correction can be performed with high precision.

In addition, the stored information may be the positional information instead of the value of the width D of the gap 401. Specifically, for example, it may be the information regarding various positions including the positions of the centers or ends of the detector modules 400-1 and 400-2, the positions of the centers or ends of respective columns of the detector modules 400-1 and 400-2, the position of the specific X-ray detection element 161, and the middle position of the group of the X-ray detection elements 161.

In the present embodiment, the manufacturing of the X-ray detector 104 and the position correction processing of the correction section 510 are performed with the opposite end of the detector module 400 to the surface adjacent to the adjacent detector module 400 as a reference position. However, the reference position is not limited to this. The reference position may be anywhere in the slice direction of the X-ray module 400. In this case, assuming that the coordinates of one reference position are X0 and the number of elements between reference positions is M, the slice position X'(n) after position correction processing of the X-ray detection element 161 located between the adjacent reference positions can be calculated by Expression (1) in the same manner as described above.

In this case, an interval between regular slice positions obtained by performing position correction processing on slices between the reference positions is different from that obtained by performing position correction processing on slices outside the region between the reference positions. Therefore, it is preferable that the reference positions 411 and 412 be set at positions between which many slices are interposed. When a gap is relatively narrow compared with the interval between slices or when there are a large number of slices in one detector module 400 and many slices can be set between the reference positions 411 and 412 accordingly, a difference in the interval between slices is small. Therefore, this is not a problem. For example, when the interval between slices L is 1 mm, the gap D is 0.1 mm, and the number of slices of the detector module 400 is 32, the reference positions 411 and 412 are set at the centers of the detector modules 400-1 and 400-2, respectively. In this case, a difference between the interval between slices outside the reference positions and the interval between slices inside the reference positions becomes about 3 μm from Expression (1). This is negligible because it is sufficiently small compared with the interval between slices L (1 mm).

In addition, the reference position may be set at different positions in the detector modules 400-1 and 400-2. Even if the reference position is set anywhere, a marker is attached near the reference position of each of the scattered-X-ray collimator 120, the scintillator element substrate 130, the photoelectric conversion substrate 140, and the wiring substrate 150, and the X-ray detector 104 is assembled with this marker as a reference, for example, when manufacturing the X-ray detector 104.

In addition, although the case of estimating the output value P'(n) after correction using a first-order polynomial in position correction is illustrated in the present embodiment, the function used for estimation of the output value P'(n) is not limited to this. For example, a second-order polynomial may be used. In this case, P'(n) can be estimated from the output values of X(n−1), X(n), and X(n+1) according to Expression (4).

[Expression 4]

$$P'(n) = P(n) - \frac{P(n)(X(n+1) - X(n-1)) + P(n+1)(X(n-1) - X(n))}{(X(n-1) - X(n))(X(n) - X(n+1))(X(n+1) - X(n-1))} (X'(n) - X(n))^2 - \frac{P(n-1)(X(n) - X(n+1))^2 - P(n)((X(n-1) - X(n))^2 + (X(n) - X(n+1))^2) + P(n+1)(X(n-1) - X(n))^2}{(X(n-1) - X(n))(X(n) - X(n+1))(X(n+1) - X(n-1))} (X'(n) - X(n))$$  (4)

In addition, other functions, such as a high-order polynomial, a trigonometric function, a logarithmic function, and an exponential function, may be used. In addition, it is also possible to determine an interpolation function using a technique, such as the spline method, and to estimate the output value P'(n). In addition, using not only the output value of the adjacent X-ray detection element 161 but also the output value of the separated X-ray detection element 161, the interpolation function may be determined by the least square method, for example, and the output value P'(n) may be estimated.

Figure 12:
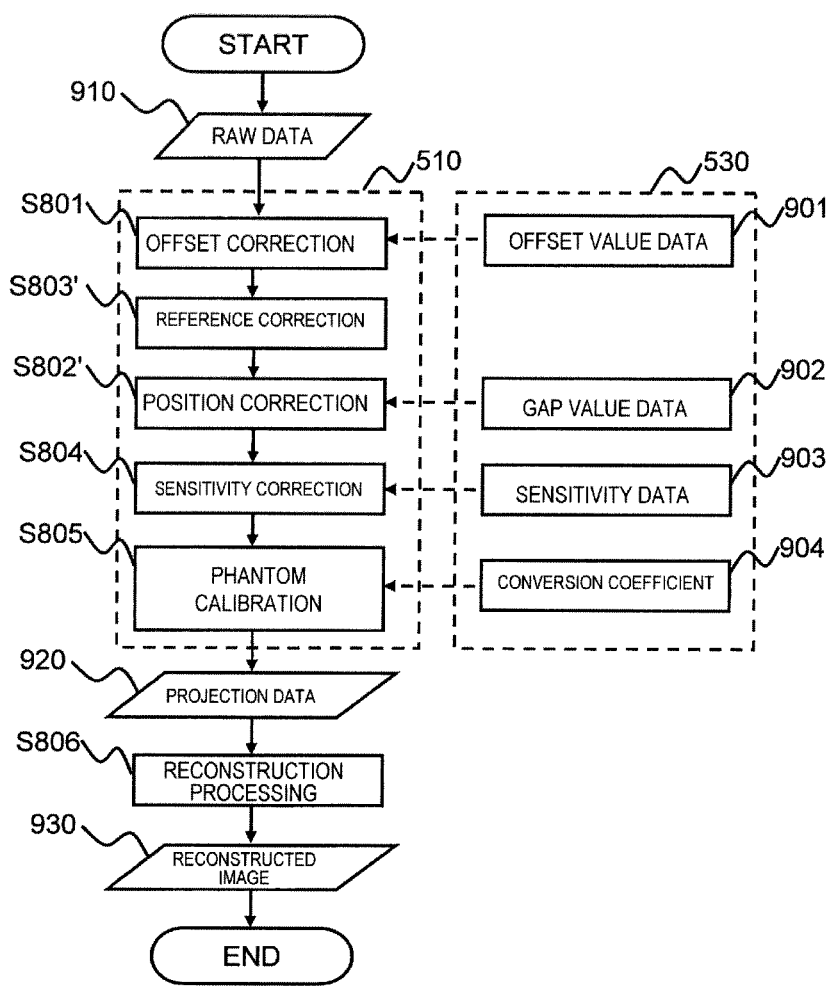
[FIG. 12]

In addition, the order of each correction processing is not limited to this, either. Although the case where the position correction processing is performed between the offset correction processing and the reference correction processing as shown in FIG. 9 has been described as an example in the present embodiment, the present invention is not limited to this. For example, position correction processing (step S802') may be performed between reference correction processing (step S803') and sensitivity correction processing (step S804), as shown in FIG. 12. This can be applied to a case where a difference in the intensity distribution of X-rays, which are irradiated from the X-ray source 100, in the slice direction 111 is small, a case where a variation in the gap between the X-ray detectors 104 is small, and the like. Moreover, in this case, in the reference correction processing (step S803'), it is not necessary to perform position correction when calculating the X-ray intensity parameter. Accordingly, since the amount of calculation can be reduced, the speed of the correction processing can be increased.

Figure 13:
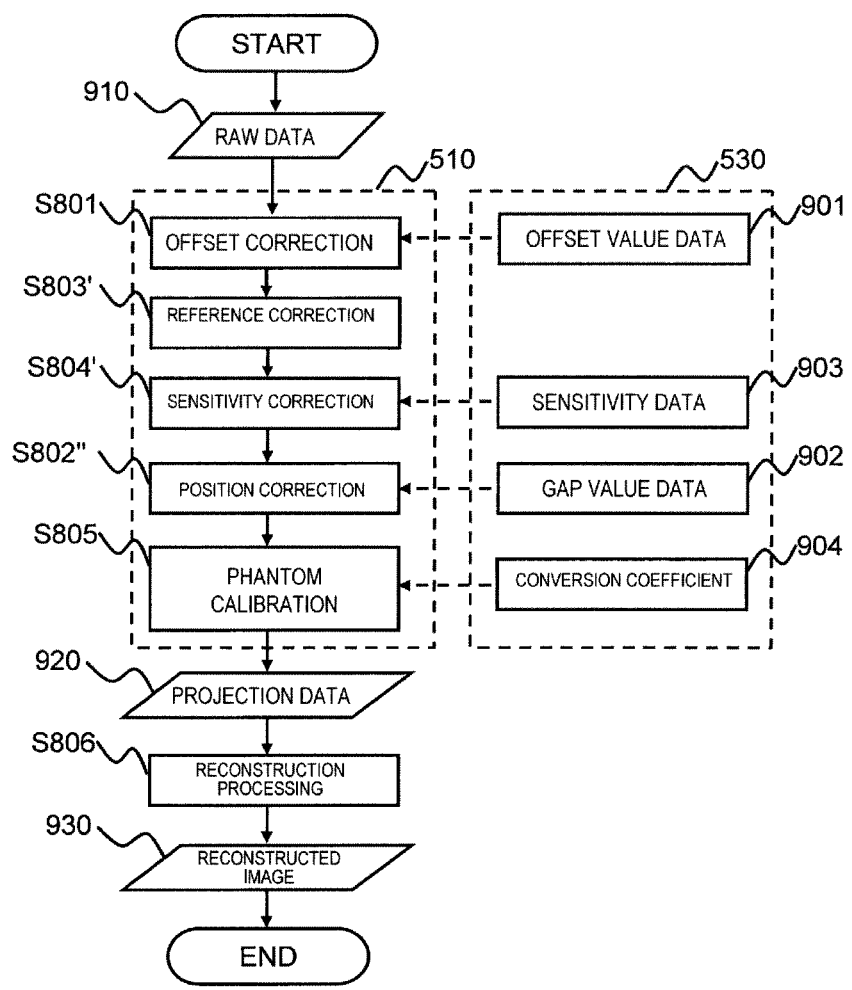
[FIG. 13]

In addition, as shown in FIG. 13, position correction processing (step S802") may be performed between sensitivity correction processing (step S804') and phantom calibration (step S805). In addition, since the sensitivity correction processing (step S804') is performed before the position correction processing (step S802") in this case, the sensitivity data 903 used in sensitivity correction is calculated without performing position correction.

Figure 14:
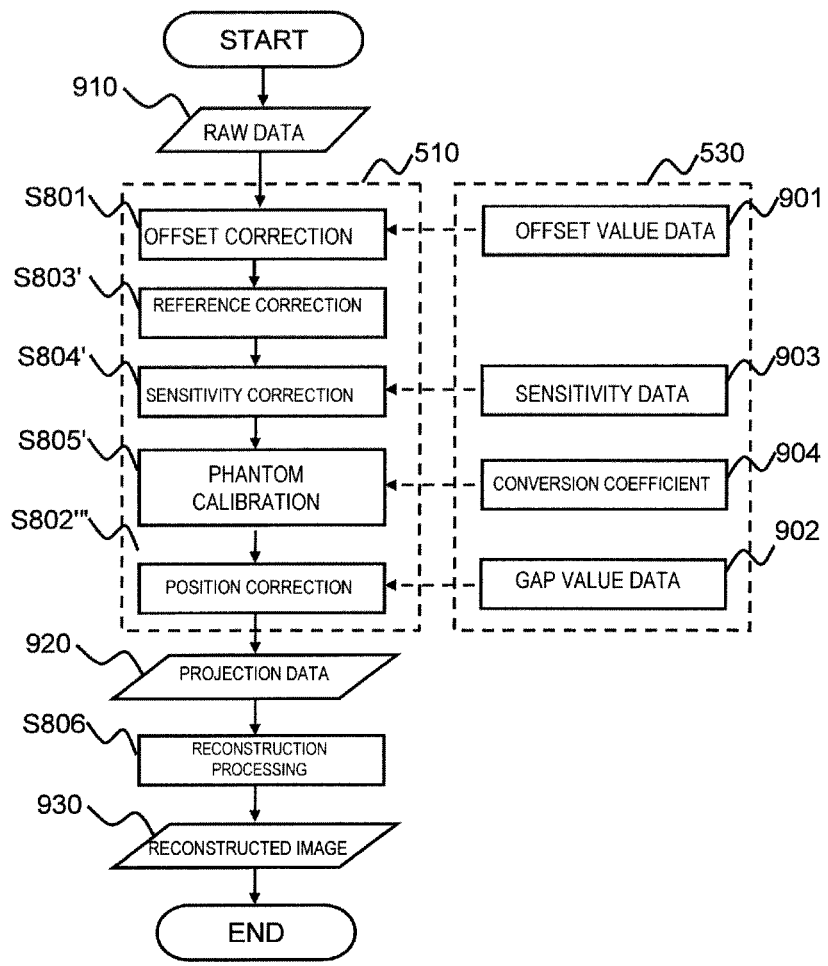
[FIG. 14]

In addition, as shown in FIG. 14, position correction processing (step S802''') may be performed after phantom calibration (step S805'). Also in this case, since the sensitivity correction processing (step S804') is performed before the position correction processing (step S802'''), the sensitivity data used in the sensitivity correction processing (step S804') is calculated without performing position correction. Similarly, also for the conversion coefficient 904, the position correction is not performed at the time of calculation.

In addition, when there is an X-ray distribution which is not uniform in the slice direction instantaneously, it is preferable to perform the position correction processing before the reference correction processing as shown in FIG. 9. Then, in the reference correction processing, reference correction can be realized with high precision even if the X-ray detector 104 which measures the X-ray intensity parameter data has the width D of the different gap 401 from the other X-ray detector 104.

Figure 15:
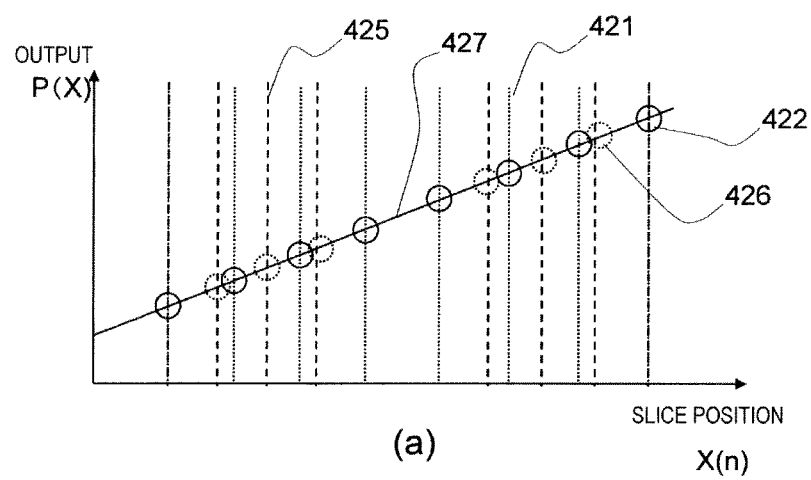
[FIG. 15]
Figure 15:
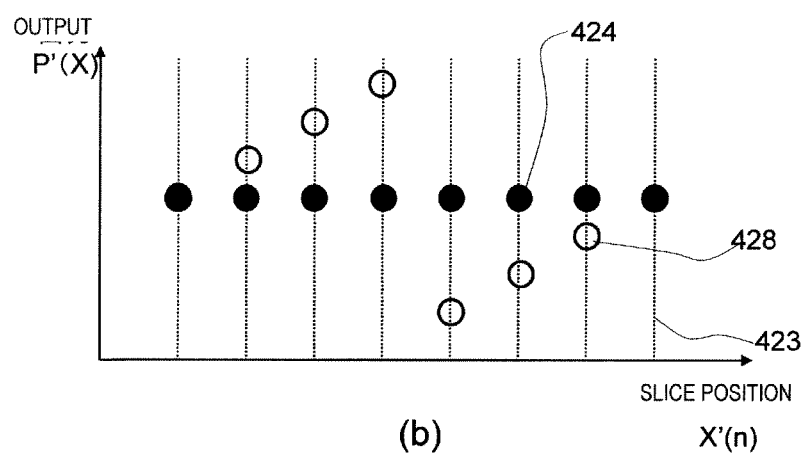

This reason will be described using FIG. 15. FIG. 15 is a view for explaining the advantages in performing position correction processing before reference correction processing. FIG. 15(a) shows an output value before position correction processing and reference correction processing, and FIG. 15(b) shows an output value after correction. In FIG. 15(a), the horizontal axis indicates the position of the X-ray detection element 161 of the X-ray detector 104, which performs actual measurement, in the slice direction 111, and this is shown by the dotted line 421. The output value is shown by the white solid circle 422. In addition, a dotted line 425 is a position of the X-ray detection element 161 of the X-ray detector 104, which acquires the X-ray intensity parameter data in reference correction processing, in the slice direction 111, and the output value is shown by a white dotted circle 426. Here, it is assumed that the X-ray detector 104 which acquires the X-ray intensity parameter data has a wide gap. Therefore, each interval between the dotted lines 421 is more equal than each interval between the dotted lines 425 is.

When the X-ray intensity has a distribution as a straight line 427 instantaneously in the slice direction 111, the output value from the X-ray detector 104 changes since X-ray sampling positions (actual slice positions) are different as shown by the white solid circle 422 and the white dotted circle 426. When the reference correction processing is performed in this state and then the position correction processing is performed, an output value difference due to the position difference remains. This becomes a different result for each slice, as shown by a white circle 428 in FIG. 15(b). On the other hand, when the position correction processing is performed first in the state of FIG. 15(a) as in the present embodiment, the slice position becomes a regular slice position which is not changed. Accordingly, the output value is almost the same. Then, when the reference correction processing is performed on the data after position correction, the output values of all slices have almost the same values as shown by a black circle 424 of FIG. 15(b). Accordingly, it can be seen that the reference correction is effective. By performing the position correction before the reference correction as described above, correction can be performed with high precision even in the case of X-ray distribution which is not uniform instantaneously in the slice direction.

In addition, all correction processings performed by the correction section 510 do not necessarily have to be performed. For example, when there is a small amount of leakage current from the photoelectric conversion element 141 and the read circuit and the offset level is small accordingly, it is not necessary to perform the offset correction processing. In addition, for example, when time variations of X-rays are small, the reference correction processing does not necessarily have to be performed. In addition, for example, when the X-ray irradiation distribution is uniform and a variation in the sensitivity of the X-ray detection element 161 is small, the sensitivity correction processing does not necessarily have to be performed. In addition, when photographing the object 102 less influenced by beam hardening, when the irradiated X-ray spectrum is close to monochrome, or in the case of measurement in which high quantification is not required for an absorption coefficient, the phantom calibration does not necessarily have to be performed. In addition, each correction processing of the offset correction processing, the reference correction processing, the sensitivity correction processing, and the phantom calibration described above may be performed using methods other than the methods described in the present embodiment, and any method may be used as long as the same effects are obtained. Moreover, for correction of raw data, correction processing other than that described above may be further performed.

Figure 16:
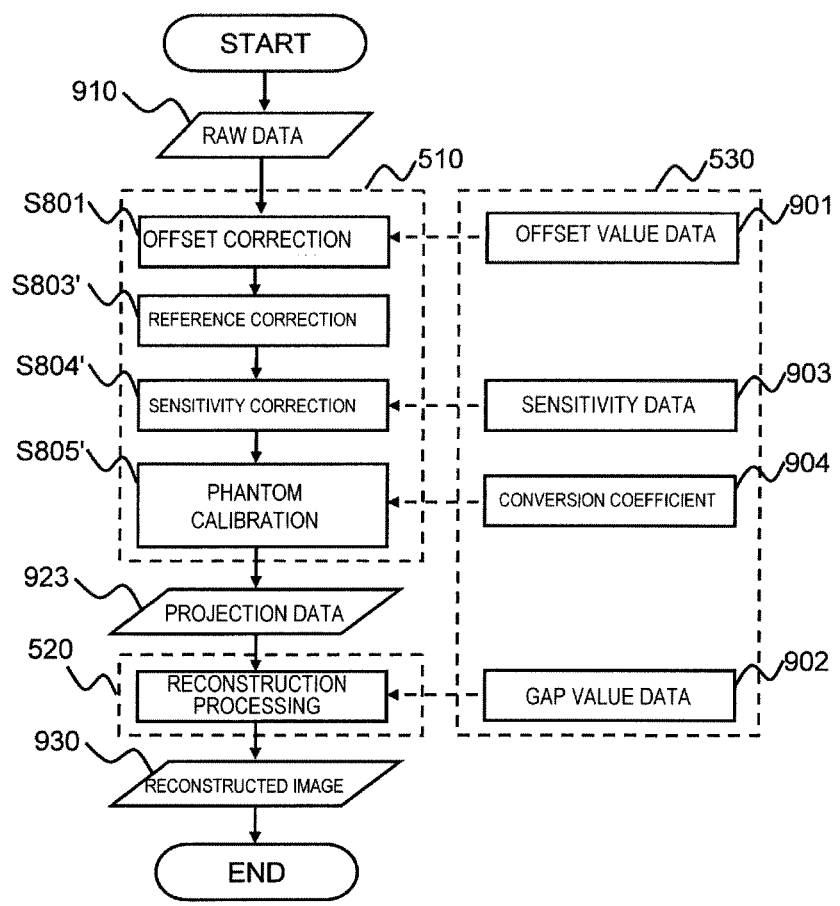
[FIG. 16]

In addition, although the correction section 510 performs the position correction processing during other correction processing in the above-described embodiment, the present invention is not limited to this. For example, the reconstruction section 520 may perform the position correction processing. The flow of processing in this case is shown in FIG. 16. As shown in this drawing, the correction section 510 performs offset correction processing (step S801), reference correction processing (step S803'), sensitivity correction processing (step S804'), and phantom calibration (step S805') to generate projection data 923. The reconstruction section 520 generates a reconstruction image while performing position correction on the acquired projection data 923 (reconstruction processing). This configuration is effective when estimating the projection data by helical scanning, for example. This will be described with reference to FIG. 17.

Figure 17:
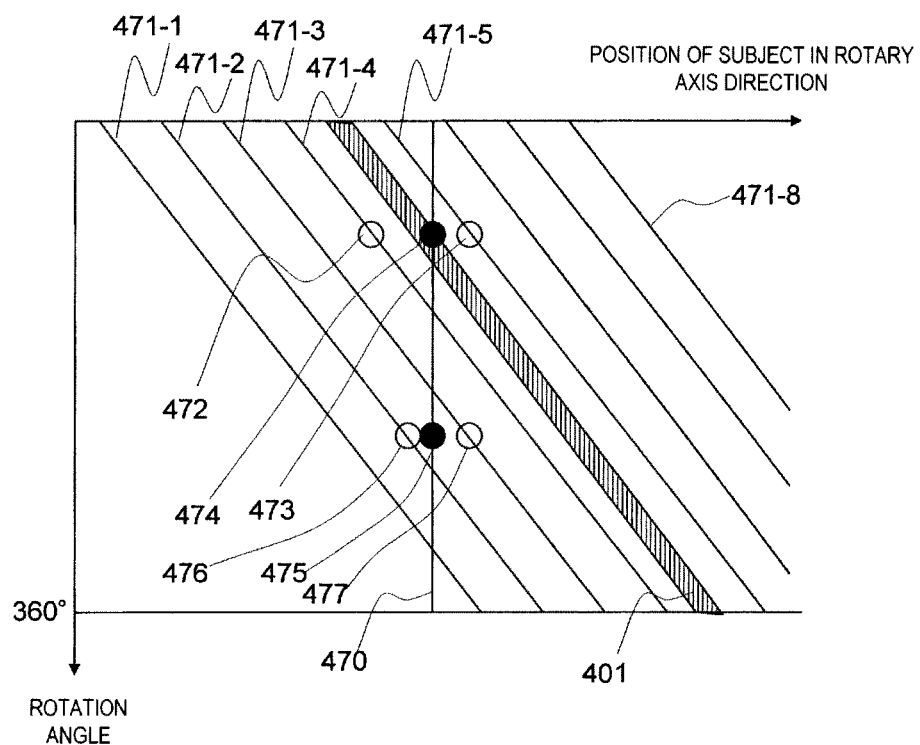
[FIG. 17]

FIG. 17 is a scanning diagram obtained by performing helical scanning. The vertical axis indicates a rotation angle of the rotating table 101 with respect to the object 102, and the horizontal axis indicates a position of the object 102 in the rotary axis direction (slice direction 111). Here, a case where the number of slices of the X-ray detector 104 is 8 is illustrated. In addition, the acquisition position (actual slice position) of actual data of an m-th (m=1, 2, ..., 8) slice is denoted as 471-m.

As shown in FIG. 17, from the acquired actual data, actual data of a plurality of slices crossing a position 470 in the drawing is used for the reconstruction image at the position 470, for example. When the position where the reconstruction image is acquired is a position where signal acquisition is not performed, such as a position 475, a signal at the position 475 is estimated from signals of a plurality of neighboring slices scanned at the same angle. Here, the signal at the position 475 is estimated by linear interpolation from a signal acquired at a position 476 of the second slice 471-2 and a signal acquired at a position 477 of the third slice 471-3, for example. Similarly, it is also necessary to estimate a signal at a position 474. For example, the signal at the position 474 is estimated by linear interpolation from a signal acquired at a position 472 of the fourth slice 471-4 and a signal acquired at a position 473 of the fifth slice 471-5, for example. At this time, using the gap value data 902, position correction is performed by performing the estimation at the coordinates in consideration of the width D of the gap 401. The estimation method described above is an example, and this is not limited to the above. For example, the estimation may also be performed using signals of three or more slices. In this case, the estimation may be performed using an interpolation function of the second-order or more polynomial. In addition, it is possible to determine a fitting function and to perform the estimation on the basis of this.

Figure 18:
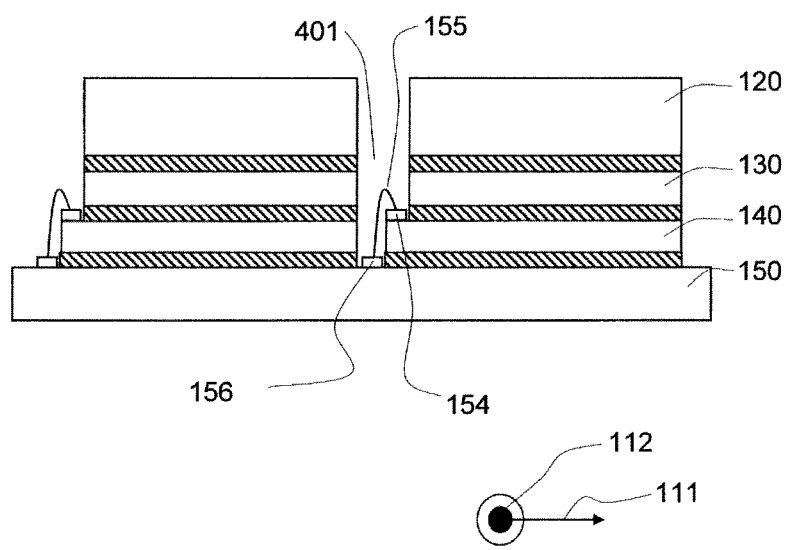
[FIG. 18]

Moreover, in the present embodiment, the photoelectric conversion substrate 140 is electrically connected to the wiring substrate 150 through its through wiring 146 on its back surface. In this case, the detector module 400 and the wiring substrate 150 are electrically connected to the electrode pads 151 and 152 with solder balls and are also fixed by bonding using the adhesive 149. However, electrical connection is not limited to this. For example, as shown in FIG. 18, it is possible to perform wiring on the surface of the photoelectric conversion substrate 140 to dispose an electrode pad 154 at the end to electrically connect the electrode pad 154 to an electrode pad 156, which is provided on the wiring substrate 150, with a bonding wire 155 or the like. In this case, the electrode pads 154 and 156 are provided within the gap 401 and are connected to each other by the bonding wire 155 within the gap 401, as shown in the drawing. Through such a configuration, tiling of the three or more detector modules 400 becomes easy in particular.

In addition, although the alignment of the scattered-X-ray collimator 120, the scintillator element substrate 130, and the photoelectric conversion substrate 140 when manufacturing the detector module 400 is partially performed using the ends of these substrates in the present embodiment, the alignment is not limited to this. In each alignment, it is possible to set a marker indicating the reference position and to perform the alignment using the marker.

Figure 19:
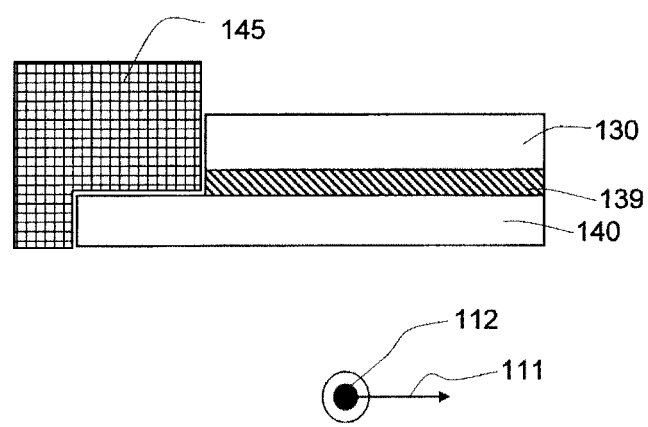
[FIG. 19]

Moreover, in the present embodiment, the alignment of the scintillator element substrate 130 and the photoelectric conversion substrate 140 and the alignment of the photoelectric conversion substrate 140 and the wiring substrate 150 are performed using markers 142 and 143, respectively. However, such alignment is not limited to this. For example, as shown in FIG. 19, a positioning jig 145 may be pressed against the ends of the photoelectric conversion substrate 140 and the scintillator element substrate 130 so that both the substrates are disposed at the desired position. This is the same as for the alignment of the photoelectric conversion substrate 140 and the wiring substrate 150. In addition, the above-described alignment method using a marker may also be used when mounting the scattered-X-ray collimator 120 on the scintillator element substrate 130.

Moreover, although the scattered-X-ray collimator 120 is provided in both directions of the channel direction 112 and the slice direction 111 in the present embodiment, the present invention is not limited to this. For example, the scattered-X-ray collimator 120 may be provided in only one of the channel direction 112 and the slice direction 111. In addition, the X-ray detector 104 may not include the scattered-X-ray collimator 120.

In addition, although the metal plate support plate 122 of the scattered-X-ray collimator 120 is provided on the surface facing the scintillator element substrate 130 in the present embodiment, the present invention is not limited to this. For example, the metal plate support plate 122 of the scattered-X-ray collimator 120 may be provided on the opposite surface, that is, a surface through which X-rays are incident on the scattered-X-ray collimator 120. In addition, the metal plate support plate 122 may be a part of the scintillator element substrate 130. For example, it may be a structure in which a groove is formed on the upper surface of the scintillator element substrate 130.

Moreover, in the present embodiment, an indirect conversion type X-ray detector which converts an X-ray into light by the scintillator element 131 and then converts the light into an electric signal by the photoelectric conversion element 141 has been described as an example of the X-ray detector 104. However, the present invention is not limited to this. For example, it is possible to use a direct conversion type X-ray detector which does not include the scintillator element substrate 130 and which converts an X-ray into an electric signal directly by the photoelectric conversion substrate 140.

In addition, although the case where the photoelectric conversion substrate 140 is crystalline silicon has been described as an example in the present embodiment, the present invention is not limited to this. As a material of the photoelectric conversion substrate 140, a photoelectric conversion material may be used. For example, germanium, cadmium tellurium, cadmium zinc tellurium, lead iodide, polysilicon, amorphous silicon, and the like may also be used.

In addition, although the reflecting material 132 is provided between the scintillator elements 131 in the present embodiment, the present invention is not limited to this. For example, a reflecting plate, such as a metal plate, may be mounted. In addition, it is possible to provide a metal plate and a plate, which has the reflecting material 132 on both the surfaces, between the scintillator elements 131. In addition, it is possible to provide the reflecting material 132 in one direction of the slice direction and the channel direction and a metal plate in the other direction. In addition, at least one of the reflecting material 132 and the metal plate may be provided in only one of the slice direction and the channel direction, and the scintillator element 131 may be connected without being cut. In addition, the scintillator element substrate 130 may be realized by one scintillator plate without being divided.

Figure 20:
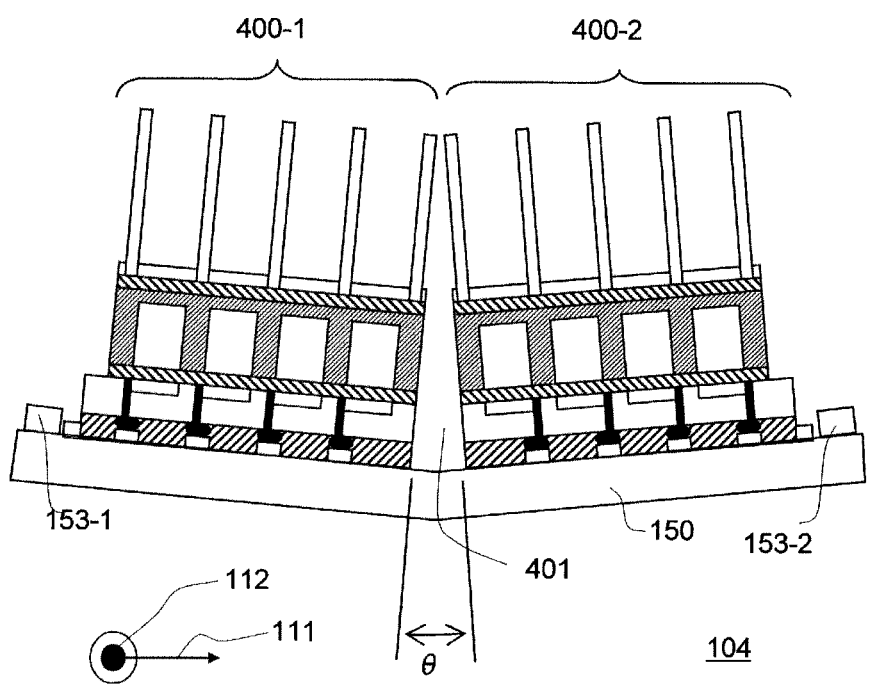
[FIG. 20]

In addition, although the case where the detector modules 400-1 and 400-2 are arrayed in parallel in the X-ray detector 104 has been described as an example in the present embodiment, the arrangement of both the detector modules 400-1 and 400-2 is not limited to this. For example, the detector modules 400-1 and 400-2 may be combined with a predetermined angle of θ in the slice direction 111, as shown in FIG. 20. Here, FIG. 20 is a sectional view at the position 1000 of FIG. 2. In addition, the wiring substrate 150 may have a step difference, and the detector modules 400-1 and 400-2 may be disposed such that the distance from the detector module 400-1 to the X-ray source 100 is different from the distance from the detector module 400-2 to the X-ray source 100.

In the present embodiment, the case where the X-ray detection elements 161 are arrayed at equal intervals in the detector module 400 has been described as an example. However, the X-ray detection elements 161 may be arrayed at unequal intervals in the detector module 400. In this case, the width D of each gap 401 is allocated so that the interval between the regular slice positions becomes the same ratio as the interval between the actual slice positions excluding the gap 401.

Figure 21:
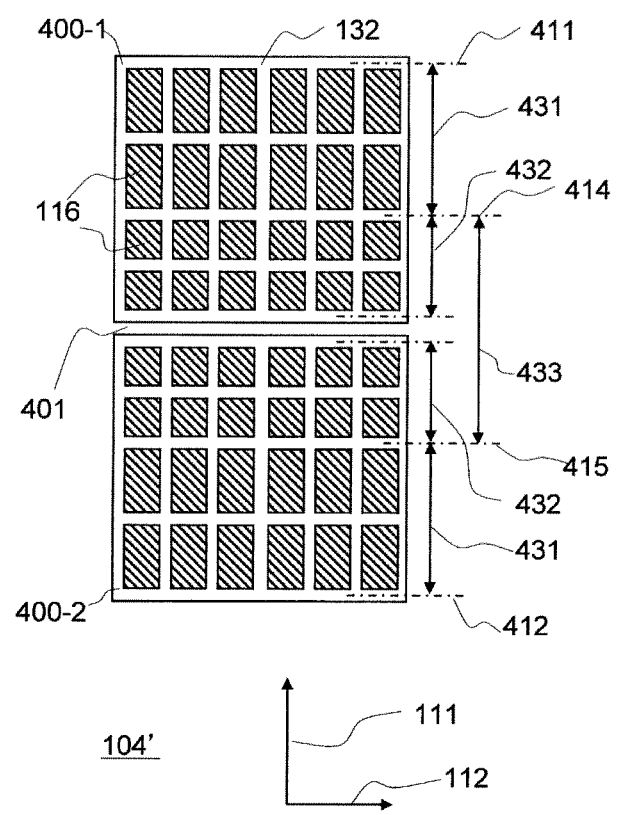
[FIG. 21]

An example of such an X-ray detector 104' is shown in FIG. 21. Here, FIG. 21 is a view when the light receiving surface of the X-ray detector 104' is seen from the X-ray incidence direction, and the detector modules 400-1 and 400-2 are adjacent to each other with the gap 401 interposed therebetween. In the slice direction 111, the X-ray detection element 161 has different widths in regions 431 and 432. Here, a case where the width of the X-ray detection element 161 in the region 432 is a half of that in the region 431.

Figure 22:
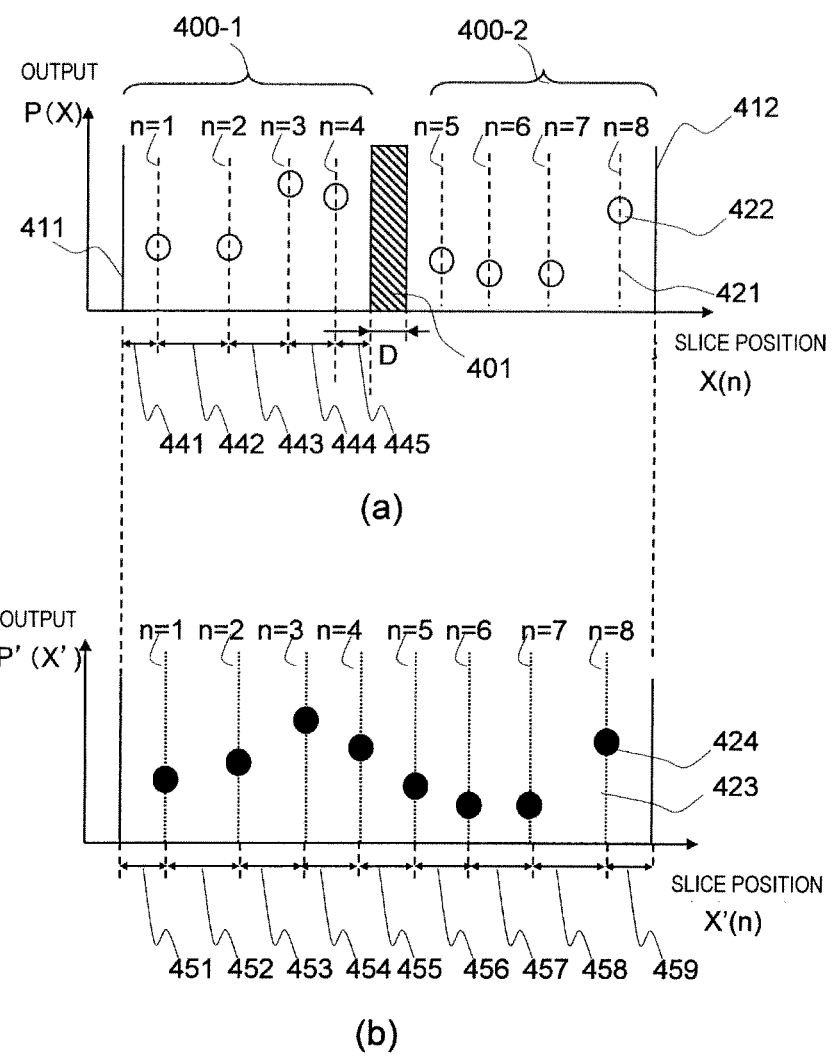
[FIG. 22]

For example, ends 411 and 412 are set as reference positions. An actual slice position and an output at this time are shown in FIG. 22(a), and a regular slice position and an output are shown in FIG. 22(b). Here, assuming that the interval between slices of the X-ray detection element 161 in the region 432 in FIG. 21 is L when the thickness of the reflecting material 132 is fixed, a distance 441 from the end 411 shown in FIG. 22 to the first slice becomes L, a distance 442 between the first and second slices becomes 2L, a distance 443 between the second and third slices becomes 1.5L, a distance 444 between the third and fourth slices becomes L, and a distance 445 between the fourth slice and the end at the gap 401 side becomes 0.5L, in the detector module 400-1. The detector module 400-2 and the detector module 400-1 are symmetrical with respect to the interface between the detector modules 400-1 and 400-2, and the detector module 400-2 has the same arrangement as the detector module 400-1 with the end 412 as a reference.

In this case, the regular slice position X' (n) is acquired by reallocating the distance between the reference positions 411 and 412 including the width D of the gap 401 while maintaining the ratio of the distances between slices when the gap 401 is removed. That is, in each distance, L is replaced with L+D/12. Accordingly, positions at which a distance 451 from the end 411 to the first slice and a distance 459 from the end 412 to the eighth slice become (L+D/12), a distance 452 between the first and second slices and a distance 458 between the seventh and eighth slices become 2×(L+D/12), a distance 453 between the second and third slices and a distance 457 between the sixth and seventh slices become 1.5×(L+D/12), and a distance 454 between the third and fourth slices, a distance 455 between the fourth and fifth slices, and a distance 456 between the fifth and sixth slices become (L+D/12) become regular slice positions.

Moreover, in the X-ray detector 104 shown in FIG. 21, positions 414 and 415 which are cut lines of the regions 431 and 432 may be set as reference positions, for example. In this case, similarly, in a region 433 between the reference positions 414 and 415, the width D of the gap 401 is allocated by the same ratio to set the regular slice position X'(n). Accordingly, in X'(n), the distances 451 and 459 are L and the distance 452 and 458 are 2L, which are the same as those before correction. On the other hand, the distances 453 and 457 are determined at positions satisfying (1.5L+D/8), and the distances 454, 455, and 456 are determined at positions satisfying (L+D/4).

Figure 23:
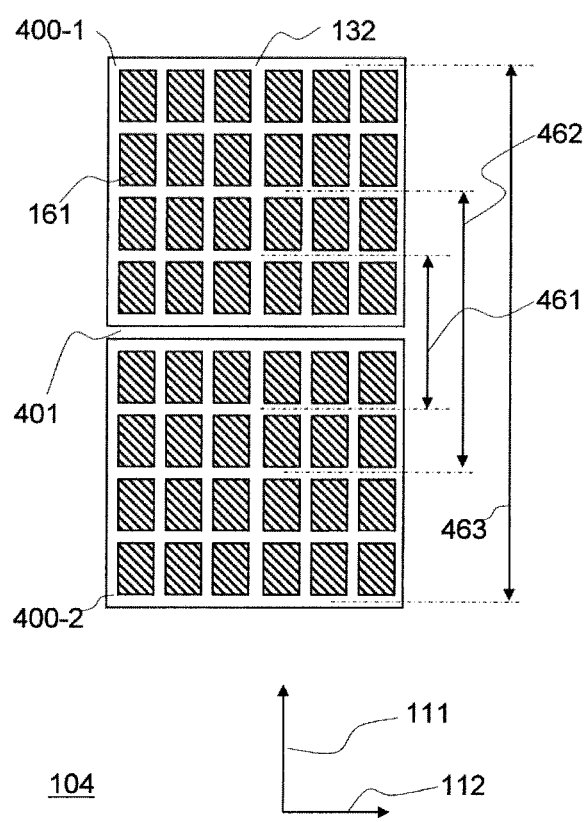
[FIG. 23]

In addition, the X-ray CT apparatus 10 of the present embodiment may be configured to further have a function of changing the X-ray irradiation range in the slice direction 111 to perform photographing. Through such a function, when the photographic range of the object 102 is narrow, it is possible to acquire an image by irradiating X-rays to only the range. As a result, an unnecessary exposure can be suppressed. Specifically, for example, the X-ray CT apparatus 10 has a function of executing by user's selection an 8-slice mode in which an image is acquired by irradiating X-rays to all slices, a 2-slice mode in which an image is acquired by irradiating X-rays to two slices, and a 4-slice mode in which an image is acquired by irradiating X-rays to four slices. The X-ray irradiation range at the time of these photographing operations will be described using FIG. 23. Here, FIG. 23 is a view showing the light receiving surface of the X-ray detector 104 seen from the X-ray incidence direction. The detector modules 400-1 and 400-2 are disposed adjacent to each other with the gap 401 interposed therebetween, the X-ray detection elements 161 for six channels and eight slices are arrayed in a two-dimensional manner.

For example, the X-ray irradiation range is a range of a region 463 shown in FIG. 23 in the case of the 8-slice mode, a region 462 in the case of the 4-slice mode, and a region 461 in the case of the 2-slice mode. In order to realize this irradiation range, the X-ray source 100 has an irradiation field changing section (not shown) for changing the irradiation field at the X-ray irradiation port, the input device 107 has a function of receiving the selection of a slice mode, the central processing unit 105 has a function of operating the controller 108 according to the received selection, and the controller 108 has a function of operating the irradiation field changing section of the X-ray source 100 according to an instruction from the central processing unit 105. When a photographer selects a slice mode through the input device 107, the input device 107 accepts the selection, and the irradiation field changing section receives the instruction through the central processing unit 105 and the controller 108 to change the X-ray irradiation field. When an instruction of X-ray irradiation is received through the input device 107 after receiving the instruction to change the X-ray irradiation field, the X-ray source 100 irradiates X-rays to the X-ray irradiation region designated previously. The signal acquisition device 109 acquires projection data from the X-ray detection element 161 in the range of X-ray irradiation.

However, the number of slice modes or the number of slices is an example, and this is not limited to the above. In addition, the X-ray irradiation range is also an example, and this is not limited to the above. For example, an X-ray irradiation range shown in FIG. 24 may be applied. That is, when the desired number of photographing slices is equal to or smaller than the number of X-ray detection elements in the slice direction provided in one detector module 400, only the X-ray detection elements 161 of the one detector module 400 may be used. Specifically, both the detector modules 400-1 and 400-2 are used in all slice modes in FIG. 23, while only one detector module 400 is used in the 2-slice mode and the 4-slice mode in FIG. 24. Thus, it becomes possible to set a photographic range not including the gap 401 by using only one detector module 400. Accordingly, the X-ray irradiation range can be made narrower by the slice width than that when the plurality of detector modules 400 is used. In addition, since X-rays irradiated to the gap 401 are not used for reconstruction of an image, the amount of X-rays not used can be reduced by setting the irradiation range so as not to include the gap 401. As a result, the use efficiency of X-rays is improved. This is particularly improved in narrow slice modes, such as a 2-slice mode.

In addition, the above-described X-ray irradiation range is an example, and the present invention is not limited to this. For example, in the 2-slice mode, two slices in the middle of either the detector module 400-1 or the detector module 400-2 may be set as the X-ray irradiation range. In addition, the region 464 in FIG. 24 may be set as the X-ray irradiation range in the 2-slice mode. In particular, it is preferable to set the X-ray irradiation range near the reference position when manufacturing the detector module 400. By setting the X-ray irradiation range near the reference position, it is possible to reduce positional deviation of the X-ray detection element 161 in each detector module 400.

Figure 24:
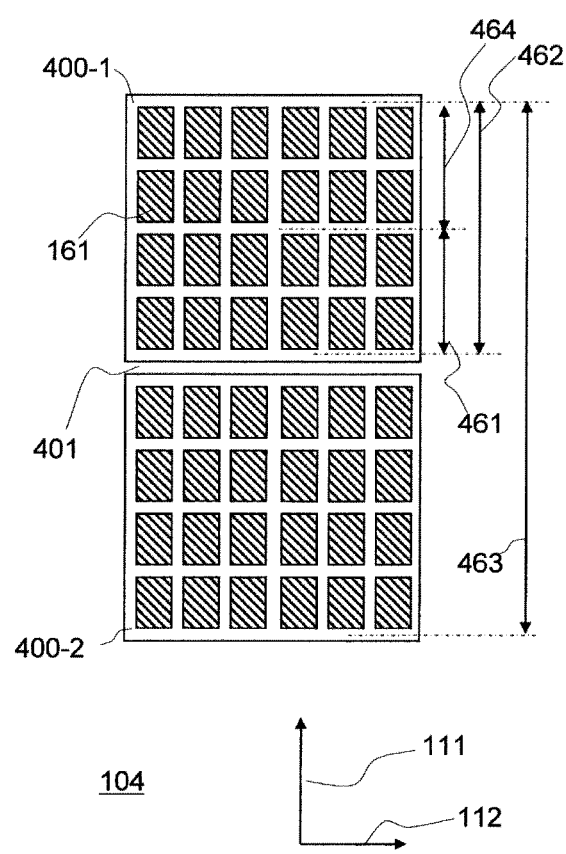
[FIG. 24]

In addition, although the case where the X-ray irradiation range is set in the detector module 400-1 is illustrated in FIG. 24, the X-ray irradiation range may also be set in the detector module 400-2. In addition, the X-ray irradiation range may be set in the different detector module 400 according to the slice mode, such that the X-ray irradiation range is set in the detector module 400-1 in the 2-slice mode and the X-ray irradiation range is set in the detector module 400-2 in the 4-slice mode.

In addition, when it is possible to set a photographic range not including the gap 401 according to the slice mode, position correction processing may not be performed according to the set slice mode. For example, whether to perform position correction processing may be registered in advance according to the slice mode, and the correction section 510 may determine whether to perform the position correction processing automatically according to the registered information to perform processing. In addition, a user may instruct whether to perform position correction processing when necessary, and the correction section 510 may determine whether to perform the position correction processing automatically according to the instruction to perform processing. Since the correction section 510 is made not to perform the position correction processing according to the slice mode, a processing time in correction processing can be shortened when the position correction processing is not performed.

In addition, although the case where the number of slices (the number of X-ray detection elements) in the slice direction 111 is the same in the plurality of detector modules 400 has been described as an example in the above embodiment, it is also possible to dispose the plurality of detector modules 400 with the different numbers of slices. For example, the detector module 400-1 with two slices, the detector module 400-2 with four slices, and the detector module 400-3 with two slices are disposed in this order in the slice direction. In addition, the X-ray irradiation ranges in the 2-slice mode and the 4-slice mode are set so as to become ranges of two slices and four slices in the detector module 400-2, respectively. In addition, the number of slices in each detector module 400 is an example, and this is not limited to the above.

In addition, as another method of setting the X-ray irradiation range not including the gap 401 in a narrow slice mode, an odd number of detector modules 400 may be disposed so that the central slice is not changed for each X-ray irradiation range. Here, the central slice is a central position of the X-ray detector 104 in the slice direction, and does not need to match an actual slice of the X-ray detector 104. That is, the central slice may not be an integer. For example, in the X-ray detector 104 with twelve slices, a 6.5-th slice between the sixth slice and the seventh slice becomes the central slice.

In such an arrangement, for example, when disposing the detector modules 400 with the same size, photographing in one detector module 400 disposed in the middle becomes possible in a slice mode, which is equal to or smaller than the number of slices that one detector module 400 has, even if the central slice is not changed. For example, when the X-ray detector 104 with twelve slices is realized by tiling the three detector modules 400 each having four slices, the X-ray irradiation ranges in the 2-slice mode and the 4-slice mode can be scanned only with the middle detector module 400.

In addition, when disposing the detector modules 400 with different sizes, it is preferable to dispose the largest detector module 400 at the central slice. Then, it is possible to realize a structure in which the gap 401 is most separated from the central slice. Therefore, even if the central slice is not changed in a narrow slice mode, photographing in one detector module 400 disposed in the middle becomes possible. For example, in the case of forming the X-ray detector 104 with twelve slices by tiling a total of three detector modules 400 with two slices, six slices, and four slices in order of slices, the gap 401 closest to the central slice is located between the eighth and ninth slices, and the X-ray irradiation ranges in the 2-slice mode (sixth and seventh slices are used) and the 4-slice mode (fifth to eighth slices are used) can be scanned only with the middle detector module 400 with six slices.

The number of slices of the X-ray detector 104 or the detector module 400 described above is an example, and various numbers of slices are possible without being limited to this. In addition, the number of detector modules 400 may also be an odd number. In addition, the number of slices in the odd number of detector modules 400 may be different.

In addition, the X-ray CT apparatus 10 of the present embodiment may be configured to further have a function of changing the slice thickness of a reconstruction image. By this function, for example, when the slice thickness of a reconstruction image realized by one slice is 0.5 mm, it is possible to obtain the slice thickness of a reconstruction image, such as 1 mm thickness of two slices, 2 mm thickness of four slices, and 4 mm thickness of eight slices. However, these slice thicknesses and the number of slices are examples, and these are not limited to the above.

Figure 25:
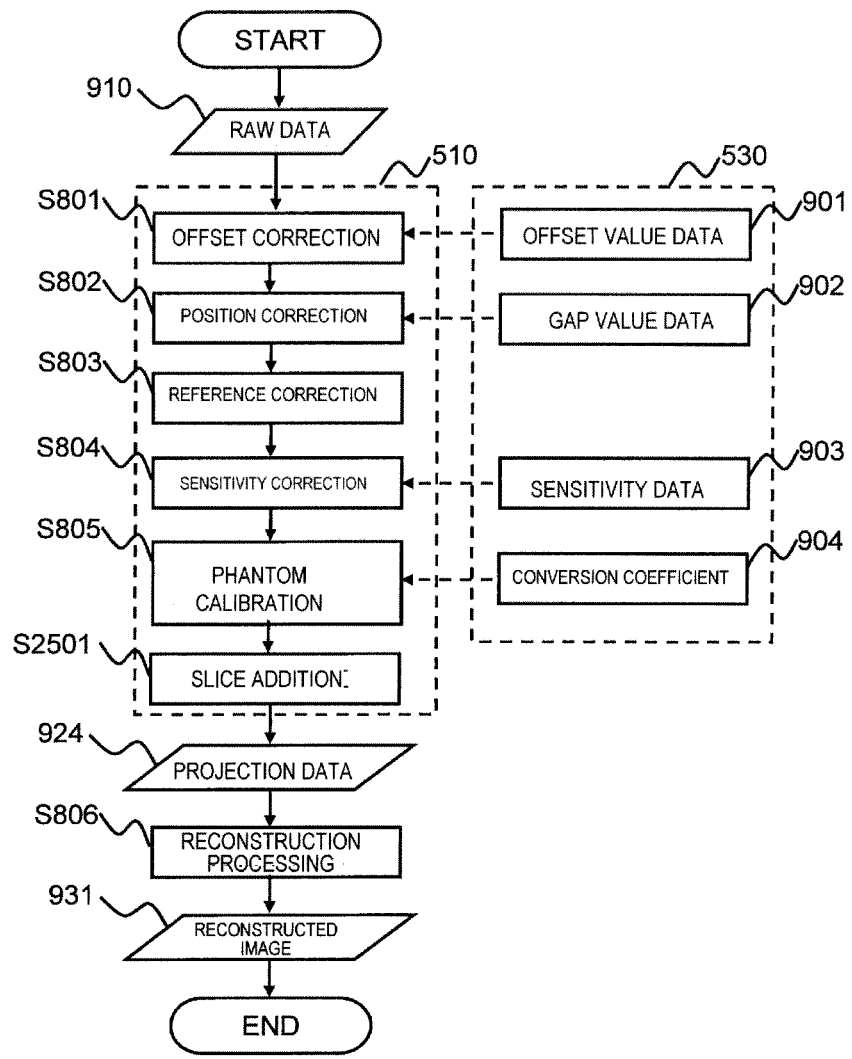
[FIG. 25]
Figure 26:
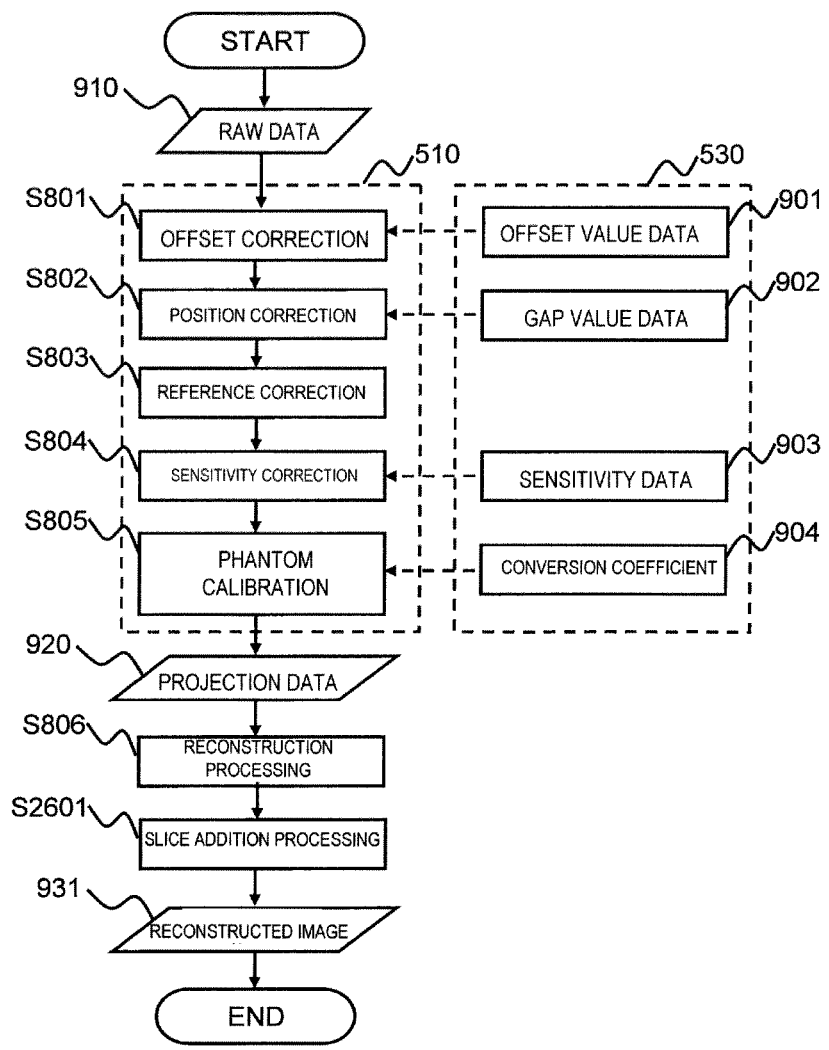
[FIG. 26]

FIGS. 25 and 26 are views for explaining an example of the flow of processing for changing the slice thickness of a reconstruction image. When there is a function of changing the slice thickness, the correction section 510 further includes a slice adding section. The slice adding section adds a predetermined number of data at the same channel position, which continues in the slice direction and which is data after all correction processings in the correction section 510 are completed, to generate projection data 924. The addition number is instructed by a user or set in advance, for example, and is stored in the correction data storage section 530. The case shown in FIG. 9 in which phantom calibration is performed as last correction processing in the correction section 510 is illustrated in FIG. 25.

As shown in this drawing, the correction section 510 performs processing until the phantom calibration as in FIG. 9 (steps S801 to S805). Then, the slice adding section performs slice addition processing (step S2501). The reconstruction section 520 performs reconstruction processing on the acquired projection data 924 (step S806) to acquire a reconstruction image 931.

As described above, in the case of generating a reconstruction image of a slice with a thickness of 1 mm when the slice thickness of a reconstruction image realized by one slice in the X-ray CT apparatus 10 is 0.5 mm, a slice adding section 180 adds the data of the X-ray detection elements 161 at the same channel positions of the first and second slices, the third and fourth slices, the fifth and sixth slices, and the seventh and eighth slices of the detector module 400, for example. Similarly, when generating a reconstruction image with a thickness of 2 mm, the slice adding section 180 adds the data of the X-ray detection elements 161 at the same channel positions of the first to fourth slices and the fifth to eighth slices of the detector module 400, for example. Similarly, when generating a reconstruction image with a thickness of 4 mm, the slice adding section 180 adds the data of the X-ray detection elements 161 at the same channel positions of all slices of the first to eighth slices of the detector module 400, for example. However, these combinations of slices are examples, and the combination of slices is not limited to these.

In addition, a timing at which the slice adding section performs slice addition processing during various correction processings performed by the respective sections of the correction section 510 does not matter. However, it is preferable to perform the slice addition processing after position correction processing in order to maintain the accuracy of position correction. This is because the number of data points in the slice direction becomes small and the information on the high spatial frequency that the data has is lost in the slice addition processing.

In addition, the slice adding section may be provided not in the correction section 510 but in the reconstruction section 520. The processing flow at this time is shown in FIG. 26. Here, a case where the processing shown in FIG. 9 is performed as correction processing until the projection data 920 is acquired is illustrated. The slice addition processing is performed after generating a reconstruction image. The reconstruction section 520 performs reconstruction processing on the projection data (step S806). Then, reconstruction images of the respective slices are added and averaged (step S2601). As a result, the reconstruction images 931 with different slice thicknesses are acquired.

<<Second Embodiment>>

A second embodiment to which the present invention is applied will be described. The X-ray CT apparatus 10 of the present embodiment has basically the same configuration as that in the first embodiment. In addition, functions of the X-ray CT apparatus 10 of the present embodiment are basically the same as those in the first embodiment. In the present embodiment, however, the X-ray detector 104 includes three or more detector modules 400 in the slice direction 111. Hereinafter, explanation will be focused on a different configuration from the first embodiment.

Here, a case where the X-ray detector 104 includes three detector modules 400-1, 400-2, and 400-3 will be described as an example. In the present embodiment, these detector modules are represented as the detector module 400 when there is no particular need to distinguish these detector modules.

Figure 27:
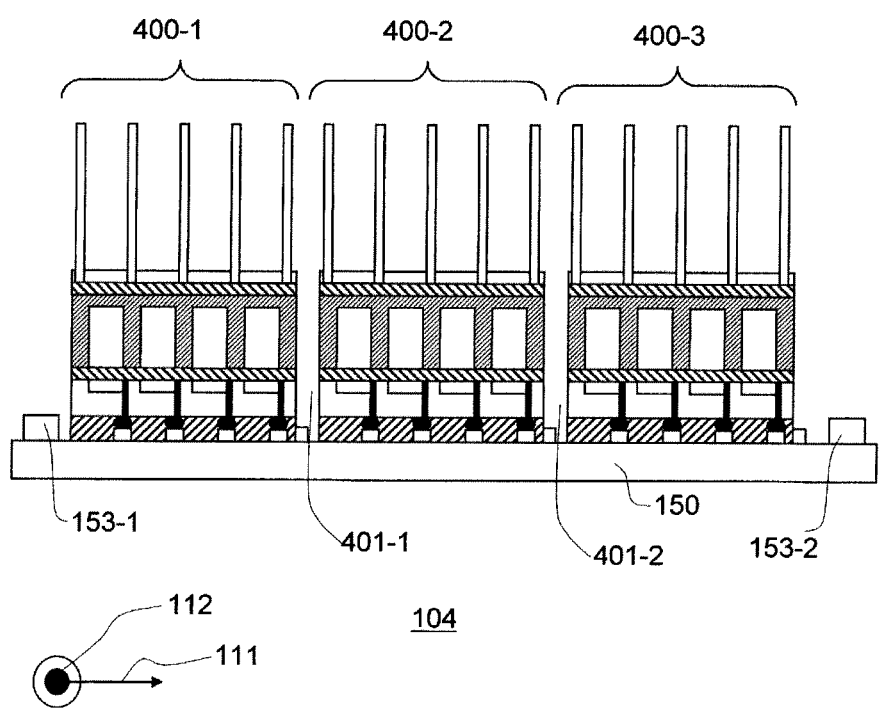
[FIG. 27]

FIG. 27 is a view showing an example of the structure of the X-ray detector 104 of the present embodiment. Here, FIG. 27 is a sectional view at the position 1000 of FIG. 2. As shown in FIG. 27, in the X-ray detector 104 of the present embodiment, the detector modules 400-1, 400-2, and 400-3 are mounted on the wiring substrate 150 with gaps 401-1 and 401-2 interposed therebetween.

Figure 28:
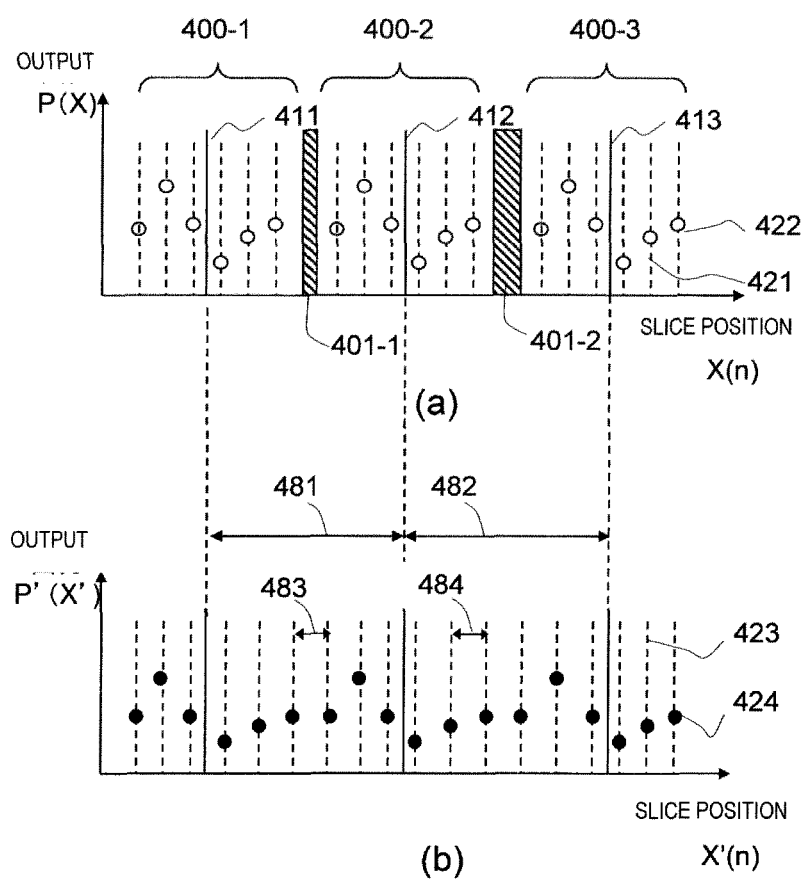
[FIG. 28]

Also in the present embodiment, the correction section 510 includes a position determining section 511' (not shown), and the regular slice position is calculated by allocating a distance of a gap to each distance between two reference positions set in advance while maintaining each ratio. Here, an example of the slice position and the output before and after position correction processing is shown in FIG. 28. FIG. 28(a) is the slice position and the output at the position before position correction processing, FIG. 28(b) is the slice position and the output at the position after position correction processing.

The X-ray detector 104 of the present embodiment sets the reference positions 411, 412, and 413 in the middle of each detector module 400. That is, the detector modules 400-1, 400-2, and 400-3 are manufactured on the basis of these reference positions 411, 412, and 413, respectively. The position determining section 511' allocates the width D1 of the gap 401-1 to each interval between the detector modules 400-1 and 400-2 while maintaining the ratio. In addition, the same processing is also performed between the detector modules 400-2 and 400-3. For example, when the X-ray detection elements 161 are arrayed at equal intervals in the detector module 400, each interval between slices 483 in a region 481 between the reference positions 411 and 412 is equal, and each interval between slices 484 in a region 482 between the reference positions 412 and 413 is also equal. Then, according to the allocation, each regular slice position X'(n) is calculated.

For example, assuming that the number of X-ray detection elements 161 between the reference positions 411 and 412 is M1, the width of the gap 401-1 is D1, the interval between the X-ray detection elements 161 is L, and the slice-direction position of the position 411 is X1 between the detector modules 400-1 and 400-2, the regular slice position X'(n) between the detector modules 400-1 and 400-2 can be calculated by the following Expression (5). In addition, the interval L between the X-ray detection elements 161 is equal within each detector module 400 and for each detector module 400 herein.

[Expression 5]

$$X'(n) = X_1 + \left(L + \frac{D1}{M1}\right)\left(n - \frac{1}{2}\right) \quad (5)$$

Similarly, assuming that the number of X-ray detection elements 161 between the positions 412 and 413 is M2, the width of the gap 401-2 is D2, the interval between the X-ray detection elements 161 is L, and the channel position of the position 412 is X2 between the detector modules 400-2 and 400-3, the regular slice position X'(n) between the detector modules 400-2 and 400-3 can be calculated by the following Expression (6). In addition, the interval L between the X-ray detection elements 161 is equal within each detector module 400 and for each detector module 400 herein.

[Expression 6]

$$X'(n) = X_2 + \left(L + \frac{D2}{M2}\right)\left(n - \frac{1}{2}\right) \quad (6)$$

Moreover, in this case, a position determined as the regular slice position X'(n) of a position other than the region between the reference positions 411 and 412 is equal to the actual slice X(n). For this reason, according to the method of the present embodiment, an interval between regular slice positions between the positions 411 and 413 is different from that outside the region between the positions 411 and 413. In addition, when the width D1 of the gap 401-1 and the width D2 of the gap 401-2 are different, an interval between slices between the reference positions 411 and 412 and an interval between slices between the reference positions 412 and 413 are also different. However, as described above, when the width of the gap 401 is relatively narrow compared with the interval between slices or when there are a large number of slices in the detector module 400 and many slices can be set between the reference positions 411 and 413 accordingly, a difference in the interval between slices is small. Therefore, this is not a problem.

The data estimating section 512 of the present embodiment performs data estimation at each slice position, which is determined using the above Expressions (5) and (6), using the same method as in the first embodiment. The correction section 510 of the present embodiment generates the projection data 920 by performing not only position correction processing but also the same various kinds of correction processing as in the first embodiment when necessary. Also in the present embodiment, the reconstruction section 520 generates a reconstruction image from the acquired projection data 920.

As described above, according to the present embodiment, even when there are three or more detector modules 400, position correction can be performed in the same manner as in the first embodiment. Therefore, as described above, when the width of the gap 401 is relatively narrow compared with the interval between slices or when there are a large number of slices in the detector module 400 and many slices can be set between the reference positions 411 and 413 accordingly, the same effects as in the first embodiment can be obtained.

In addition, according to the present embodiment, the reference position is set for each detector module 400. Therefore, even when the three or more detector modules 400 are tiled, equal-interval data can be estimated using the gap value data 902 between the adjacent reference positions for every adjacent reference positions. Thus, it is possible to prevent a lowering in data estimation accuracy due to the accumulation of errors of the manufacturing accuracy or the measurement accuracy. That is, according to the present embodiment, for example, when the first to third detector modules are tiled, data estimation between the first and second detector modules is determined by the manufacturing accuracy or the measurement accuracy of a gap or the width of an X-ray detection element between the first and second detector modules and is not influenced by the manufacturing accuracy or the measurement accuracy of a gap between the second and third detector modules or the width of an X-ray detection element in the third detector module.

In addition, although the case where the number of detector modules 400 mounted in the slice direction 111 is three has been described as an example in the present embodiment, the above processing can be performed similarly even if the number of detector modules 400 is four or more.

In addition, although the reference position is set as the center of each detector module 400 in the present embodiment, the reference position is not limited to this. Any position in each detector module 400 may be set as the reference position. In addition, the reference position may be set at different position in each detector module 400.

In addition, even if the width of a gap between the detector modules 400 is different, regular slice positions may be determined such that the same slice interval is set for all slices between the reference positions. A method of determining the interval between slices by the position determining section 511 in this case will be described using FIG. 29. FIG. 29(a) shows "before position correction processing", and FIG. 29(b) shows "after position correction". In addition, the interval between the X-ray detection elements 161 shown in FIG.

29(a) is equal within each detector module 400 and for each detector module 400. Hereinafter, a case where three detector modules 400-1, 400-2, and 400-3 are provided will be described as an example.

Here, as shown in FIG. 29, in the detector modules 400 disposed at both ends in the slice direction 111 in the X-ray detector 104, that is, in the detector modules 400-1 and 400-3, slice positions of the ends of the detector modules 400-1 and 400-3 not facing the other detector modules 400 are set as the reference positions 411 and 413. In addition, the reference position 412 of another detector module (here, the detector module 400-2) is set such that the width of a gap with respect to the number of slices between the reference positions becomes equal in each detector module 400.

For example, assuming that the number of slices between the reference positions 411 and 412 is M1, the number of slices between the reference positions 412 and 413 is M2, the design value of the width of the gap 401-1 is D1, and the design value of the width of the gap 401-2 is D2, the reference position 412 is set so as to satisfy Expression (7). Here, M1 and M2 do not need to be integers, and the reference position 412 may be set between slices.

[Expression 7]

$$\frac{D1}{M1} = \frac{D2}{M2} \quad (7)$$

Here, it is assumed that each detector module 400 has the same configuration, for example, the interval between slices of the X-ray detection element 161 before correction is L and the number of slices is N. If the position of the position reference 412 is calculated using Expression (7), the length H from the end adjacent to the detector module 400-1 to the distance 485 of the reference position 412 can be calculated by Expression (8).

[Expression 8]

$$H = \frac{2D1 - D2}{D1 + D2} NL \quad (8)$$

Accordingly, from Expression (8), the widths D1 and D2 of gaps should be in the range of 0.5D2 ≤D1 D2 in order to realize the reference position 412 in the detector module 400-2.

For example, when the width DI of the gap 401-1 is 0.1 mm, the width D2 of the gap 401-2 is 0.15 mm, the number of slices N of each detector module 400 is 32, and the interval L between the X-ray detection elements 161 before correction is 1 mm as the design values of the X-ray detector 104, the distance H is calculated as 6.4 mm. Accordingly, in this case, the reference position 412 of the detector module 400-2 is set at the place distant by 6.4 mm from the end adjacent to the detector module 400-1.

When the reference position is set as described above, the design values may be used as the gap value data 902 of the gaps 401-1 and 401-2 or actual measurement values may be used in the same manner as in the first embodiment at the time of position correction processing by the correction section 510.

In addition, although the case where the interval between the X-ray detection elements 161 is equal within each detector module 400 and for each detector module 400 is illustrated in FIG. 29, this method is not limited to this. For example, the method may also be applied to a case where the interval between the X-ray detection element 161 is different within each detector module 400 or a case where the interval between the X-ray detection element 161 differs according to each detector module 400. In this case, in order to make the width of a gap with respect to the number of slices between the reference positions equal in each detector module 400, it is preferable to set the reference position 412 such that the ratio of the distance between the adjacent reference positions 411 and 412 and the distance between the adjacent reference positions 413 and 412 becomes equal to the ratio between the design value D1 of the width of the gap 401-1 and the design value D2 of the width of the gap 401-2. That is, it is preferable to satisfy Expression (9) when the distance between the reference positions 411 and 412 is set to L1 and the distance between the reference positions 413 and 412 is set to L2. In addition, it can be seen that Expression (9) becomes equal to Expression (7) under the conditions in which the interval between the X-ray detection elements 161 is fixed.

[Expression 9]

$$\frac{D1}{L1} = \frac{D2}{L2} \quad (9)$$

By using the above-described method, also in three or more detector modules 400, the slice position which is approximately the same as when the detector modules 400 are tiled without a gap can be realized without causing a lowering in the estimation accuracy due to the accumulation of errors of the manufacturing accuracy or the measurement accuracy.

In addition, although the slice positions at both ends are set as the reference positions 411 and 413 of the detector modules 400-1 and 400-3 disposed at both ends in the slice direction in this method, the present invention is not limited to this. Assuming that the number of slices between the reference positions 411 and 412 is M1, the number of slices between the reference positions 412 and 413 is M2, the design value of the width of the gap 401-1 is D1, and the design value of the width of the gap 401-2 is D2, the reference position 412 is preferably set so as to satisfy Expression (9).

In addition, the number of detector modules disposed in the slice direction is not limited to three, and four or more detector modules may also be disposed. In this case, assuming that the number of slices between the reference position of the i-th (i is a natural number of 4 or more) detector module 400-i and the reference position of the (i+1)-th detector module 400-(i+1) is Mi and the width of the gap between the detector module 400-i and the detector module 400-(i+1) is Di, each reference position is preferably set such that Di/Mi is fixed.

In addition, also in the present embodiment, various modifications which are applicable in the first embodiment may be applied.

In each of the embodiments described above, the X-ray CT apparatus for medical applications is described as an example. However, the present invention is not limited to this. The present invention may be applied to all CT apparatuses in which the X-ray detector 104 and the correction section 510 are provided. For example, a CT apparatus for non-destructive inspections, an X-ray cone beam CT apparatus, and a dual energy CT apparatus may also be used.

In addition, the present invention is not limited to each embodiment described above, and various modifications may be made within the scope without departing from the scope and spirit of the present invention in the phase of implementation. In addition, various phases are included in each embodiment described above, and various inventions may be extrapolated by proper combination of the plurality of components disclosed. For example, some components may be excluded from all the components shown in each embodiment.

As described above, according to the X-ray CT apparatus of each of the above embodiments, the artifact in a reconstruction image caused by characteristic degradation of the X-ray detector 104, which occurs due to aligning the X-ray detectors 104 densely, or by positional deviation of an X-ray detection element, which occurs when manufacturing or installing the X-ray detector 104, can be reduced or eliminated by correcting the projection data. In addition, since the workability in aligning the X-ray detectors 104 can be improved, the X-ray detectors 104 can be tiled cheaply and easily.

Accordingly, tiling of the detector modules 400 becomes possible without making small the photoelectric conversion element 141 or the scintillator element 131 of the X-ray detection element 161 at the end of the X-ray detector 104 or without making a separator or a reflecting layer thin. As a result, the same signal as when the X-ray detection element 161 is formed by one detector module 400 can be acquired while suppressing a lowering in the light receiving efficiency or the X-ray use efficiency, a lowering in the light collection efficiency, increases in these variations, and the like.

In addition, since a space may be provided between the photoelectric conversion element 141 and the end of the photoelectric conversion substrate 140 when necessary, it is possible to dispose the photoelectric conversion element 141 in a region where a crack or the like made when machining the end is not present. Therefore, since the dark current characteristics or the photoelectric conversion efficiency of the photoelectric conversion element 141 at the end are improved, these variations can be reduced.

In addition, when mounting the scattered-X-ray collimator 120, it is not necessary to make thin the metal plate 121 which forms the scattered-X-ray collimator 120. Since the metal plate 121 with a sufficient thickness can be used, a lowering in the scattered ray removal efficiency can be prevented. In addition, since the gap 401 between the detector modules 400 can be set according to the required width, the metal plate 121 can be supported stably.

In addition, the X-ray CT apparatus 10 of each embodiment described above includes alignment means for determining the installation position of the detector module 400 at the reference positions, which are set in the middle of the detector module 400, the opposite end to the adjacent surface, and the like, when manufacturing the X-ray detector 104, and the gap 401 with a required width is provided between the detector modules 400. Through such a structure, since the position of the detector module 400 can be determined by the alignment means without depending on a state of the end of the detector module 400 facing the adjacent surface, the position of the detector module 400 can be accurately determined. Here, examples of the state of the end of the detector module 400 include the flatness or linearity of a semiconductor substrate, a scintillator substrate, and a collimator, variations in manufacturing dimensions, and the existence of irregularities.

As described above, according to each of the above embodiments, it is possible to provide an X-ray CT apparatus that can reduce or eliminate the artifact in a reconstruction image caused by characteristic degradation of X-ray detectors, which occurs due to aligning the X-ray detectors densely, or by positional deviation of X-ray detection elements, which occurs when manufacturing or installing the X-ray detectors, by correcting the projection data, that can improve the workability in aligning the X-ray detectors, and in which the X-ray detectors can be cheaply tiled.

REFERENCE SIGNS LIST

10: X-ray CT apparatus
100: X-ray source
101: rotating body
102: object
103: top plate
104: X-ray detector
105: central processing unit
106: display device
107: input device
108: controller
109: signal acquisition device
111: rotary axis direction, slice direction
112: rotation direction, channel direction
120: scattered X-ray collimator
121: metal plate
122: metal plate support plate
123: recess
124: groove
129: adhesive
130: scintillator element substrate
131: scintillator element
132: light reflecting material
139: adhesive
140: photoelectric conversion substrate
141: photoelectric conversion element
146: through wiring
142: marker
143: marker
144: end
145: positioning jig
149: adhesive
150: wiring substrate
151: electrode pad
152: electrode pad
153: connector
155: bonding wire
156: electrode pad
157: electrode pad
159: fixing hole
160: X-ray detection element substrate
161: X-ray detection element
201: thickness of a light reflecting material
202: thickness of an end light reflecting material
203: distance between scintillator elements
204: distance from end scintillator element to end of a detector module
205: scintillator element width
206: end scintillator element width
211: center
212: inter-element distance in a module
213: inter-element distance between modules
214: between metal plates
300: simulator
310: X-ray absorption coefficient value
320: absorption rate calculation
400: detector module
401: gap
411: reference position
412: reference position 413: reference position
414: reference position
415: reference position
421: slice position
422: output value
423: slice position
424: output value
425: slice position
426: output value
427: X-ray intensity distribution
428: output value
431: region
432: region
433: region
441: distance
442: distance
443: distance
444: distance
445: distance
451: distance
452: distance
453: distance
454: distance
455: distance
456: distance
457: distance
458: distance
459: distance
461: X-ray-irradiation region
462: X-ray-irradiation region
463: X-ray-irradiation region
464: X-ray-irradiation region
470: reconstruction position
471: actual slice position
472: position
473: position
474: position
475: position
476: position
477: position
481: between reference positions
482: between reference positions
483: interval between slices
484: interval between slices
485: distance
510: correction section
511: position determining section
512: data estimating section
513: correction data obtaining section
520: reconstruction section
530: correction data storage section
701: solid line
702: dotted line
901: offset value data
902: gap value data
903: sensitivity data
904: conversion coefficient
910: raw data
911: raw data
912: raw data
920: projection data
921: projection data (calculation value)
922: projection data
923: projection data
924: projection data
930: reconstruction image
931: reconstruction image

The invention claimed is;

1. An X-ray CT apparatus comprising:
X-ray generation means configured to irradiate X-rays;
an X-ray detector in which a plurality of detector modules, each of which includes X-ray detection elements that detect the X-rays and convert the X-rays into electric signals and that are aligned in a two-dimensional direction of a channel direction and a slice direction, are arrayed in the slice direction;
signal processing means configured to generate projection data by performing signal processing on raw data acquired from the electric signals detected by the plurality of X-ray detection elements of the X-ray detector; and
reconstruction processing means configured to generate a reconstruction image by performing reconstruction processing on the projection data,
wherein each of the detector modules has reference positions at predetermined positions in the slice direction,
in the detector modules, there is a gap between the detector modules adjacent to each other in the slice direction, and
the signal processing means includes storage means configured to store the width of the gap in the slice direction as a gap value, position correction means configured to correct a slice position, which is specified by a position of the X-ray detection element of the X-ray detector, to a position set in advance between the reference positions set in two of the plurality of detector modules, and data estimation means configured to estimate a data output value at a slice position after correction by the position correction means from the gap value stored in the storage means and the raw data acquired from the electric signals detected by the X-ray detection elements and generates the projection data from the data output value estimated by the data estimation means.

2. The X-ray CT apparatus according to claim 1,
wherein the position correction means calculates the slice position after correction by allocating the width of the gap between the reference positions such that slice positions are arrayed while maintaining an interval ratio between the X-ray detection elements when the gap is not present.

3. The X-ray CT apparatus according to claim 2,
wherein the intervals between the X-ray detection elements in the detector module are equal.

4. The X-ray CT apparatus according to claim 3,
wherein assuming that an interval between X-ray detection elements in the plurality of detector modules is L, a sum of the gap values between the plurality of detector modules between the reference positions is D, the total number of X-ray detection elements in the slice direction between the reference positions is M (M is a natural number), and a slice-direction position of one of the reference positions is X0, the position correction means corrects an n-th (n is a natural number of M or less) slice position from the reference position in the slice direction to $X0+(L+D/M)\times(n-1/2)$.

5. The X-ray CT apparatus according to claim 1,
wherein the data estimation means estimates the data output value by interpolation from the raw data between the reference positions.

6. The X-ray CT apparatus according to claim 5,
wherein the data estimation means determines a polynomial, which has a slice-direction position as a variable, using the raw data between the reference positions plurally and estimates the data output value from the polynomial.

7. The X-ray CT apparatus according to claim 1,
wherein the signal processing means further includes reference correction means for correcting a temporal change in X-ray intensity, and
the reference correction means calculates an X-ray intensity parameter, which is used for the correction, using the output value after correction and also performs the correction.

8. The X-ray CT apparatus according to claim 1, further comprising:
rotational driving means configured to perform rotational driving around an object in a state where at least one X-ray detector is mounted;
a bed on which the object is mounted;
moving means configured to move the rotational driving means and the bed relatively in a rotary axis direction of the rotational driving means; and
reconstruction position determination means configured to determine a reconstruction position of the object, at which a reconstruction image is generated, from the raw data acquired by the movement, and
the data estimation means further estimates the data output value at the reconstruction position determined by the reconstruction position determination means from the gap value stored in the storage means and the raw data acquired from the electric signals detected by the X-ray detection elements.

9. The X-ray CT apparatus according to claim 1,
wherein two of the detector modules are detector modules disposed at both ends in the slice direction.

10. The X-ray CT apparatus according to claim 9,
wherein the reference position is set at an opposite slice-direction end of each of the two detector modules, which are disposed at both the ends, to the other adjacent detector module.

11. The X-ray CT apparatus according to claim 1,
wherein three or more detector modules are provided,
two of the detector modules are detector modules adjacent to each other in the slice direction, and
the reference position is set at a position at which a ratio between an interval between reference positions of the adjacent detector modules and a gap value between the adjacent detector modules is fixed.

12. The X-ray CT apparatus according to claim 1,
wherein the plurality of detector modules are disposed in the slice direction in a state fixed to support means, and
the support means includes alignment means at a position corresponding to the reference position of the detector module fixed to the support means.

13. The X-ray CT apparatus according to claim 1,
wherein the detector module includes:
a scintillator element substrate on which a plurality of scintillator elements that convert the X-rays into light are arrayed in the slice direction with a light reflecting layer interposed therebetween;
a photoelectric conversion substrate on which a plurality of photoelectric conversion elements that convert the light into electric signals are arrayed in the slice direction; and
a scattered X-ray collimator in which a plurality of shielding plates that shield the X-rays are arrayed in parallel in the slice direction at predetermined intervals, and
the scattered X-ray collimator, the scintillator element substrate, and the photoelectric conversion substrate are laminated in this order with the reference position as a reference such that the shielding plate and the light reflecting layer face each other.

14. The X-ray CT apparatus according to claim 13,
wherein the scattered X-ray collimator includes shielding plate support means that supports the shielding plate, and
the shielding plate support means has a structure protruding from the shielding plate toward an adjacent detector module at an end of each detector module adjacent to another detector module.

15. The X-ray CT apparatus according to claim 1, further comprising:
irradiation region changing means configured to change a region to which the X-rays are irradiated by the X-ray generation means between a first irradiation field, which is a range over the plurality of detector modules, and a second irradiation field, which has a different central slice position from the first irradiation field and which is an entire or partial range of the one detector module.

16. The X-ray CT apparatus according to claim 1,
wherein the X-ray detector includes the odd number of three or more detector modules,
at least one of the odd number of three or more detector modules has a different length in the slice direction, and
a gap between the detector modules is disposed at a different position from a central slice position of the X-ray detector.

17. The X-ray CT apparatus according to claim 16,
wherein the X-ray detector has a structure in which the longest X-ray detection module in the slice direction is disposed at the central slice position of the X-ray detector.

18. The X-ray CT apparatus according to claim 1, further comprising:
slice addition means configured to add at least one of the projection data and the reconstruction image by the number of slices set in advance in the slice direction.

* * * * *